US011123153B2

(12) United States Patent
Davis et al.

(10) Patent No.: US 11,123,153 B2
(45) Date of Patent: Sep. 21, 2021

(54) METHOD AND SYSTEM FOR ENSURING AND TRACKING HAND HYGIENE COMPLIANCE

(71) Applicant: Sage Products, LLC, Cary, IL (US)

(72) Inventors: Gregory T. Davis, Cary, IL (US); David Beck, Cary, IL (US); Ronald C. Cagle, Cary, IL (US); Jessica Farrell, Cary, IL (US)

(73) Assignee: Sage Products, LLC, Cary, IL (US)

( * ) Notice: Subject to any disclaimer, the term of this patent is extended or adjusted under 35 U.S.C. 154(b) by 1012 days.

(21) Appl. No.: 14/604,207

(22) Filed: Jan. 23, 2015

(65) Prior Publication Data

US 2015/0134357 A1 May 14, 2015

Related U.S. Application Data

(63) Continuation-in-part of application No. 14/029,746, filed on Sep. 17, 2013, now Pat. No. 10,121,149.

(Continued)

(51) Int. Cl.
*A47K 5/122* (2006.01)
*G16H 40/20* (2018.01)
(Continued)

(52) U.S. Cl.
CPC .............. *A61B 90/80* (2016.02); *A47K 5/122* (2013.01); *A61B 90/98* (2016.02); *G06Q 30/018* (2013.01); *G16H 40/20* (2018.01)

(58) Field of Classification Search
None
See application file for complete search history.

(56) References Cited

U.S. PATENT DOCUMENTS

RE37,675 E    4/2002  Gueret
6,392,546 B1  5/2002  Smith
(Continued)

FOREIGN PATENT DOCUMENTS

WO    2004052162 A1    6/2004
WO    2013106440 A1    7/2013

OTHER PUBLICATIONS

Boyce, Hand hygiene compliance monitoring: current perspectives from the USA, 2008, J. Hospital Infection, 70(S1), p. 2-7 (Year: 2008).*

(Continued)

*Primary Examiner* — Gregory Lultschik
*Assistant Examiner* — William G Lultschik
(74) *Attorney, Agent, or Firm* — Foley & Lardner LLP

(57) ABSTRACT

A method for ensuring hand hygiene compliance may include tracking dispensing of a plurality hand hygiene dispensers having hand sanitizer. Each hand hygiene dispenser can be associated with an individual user. A processor may determine dispensing rates of the plurality of hand hygiene dispensers for a plurality of predetermined time periods and each of the plurality of the hand hygiene dispensers is identified with an individual user. The average dispensing rate can be calculated taking a predetermined number of highest dispensing rates out of the plurality of predetermined time periods. The rates can be displayed to the users, and the users can be notified of proper hand hygiene compliance or if the average dispensing rate falls below a target threshold rate.

24 Claims, 32 Drawing Sheets

Related U.S. Application Data

(60) Provisional application No. 61/702,013, filed on Sep. 17, 2012.

(51) Int. Cl.
    *A61B 90/80*     (2016.01)
    *G06Q 30/00*     (2012.01)
    *A61B 90/98*     (2016.01)

(56) References Cited

U.S. PATENT DOCUMENTS

| | | |
|---|---|---|
| 6,727,818 B1 | 4/2004 | Wildman et al. |
| 6,882,278 B2 | 4/2005 | Winings et al. |
| 6,883,563 B2 | 4/2005 | Smith |
| D512,648 S | 12/2005 | Smith et al. |
| 6,975,231 B2 | 12/2005 | Lane et al. |
| 7,015,816 B2 | 3/2006 | Wildman et al. |
| 7,372,367 B2 | 5/2008 | Lane et al. |
| 7,375,640 B1 | 5/2008 | Plost |
| 7,408,470 B2 | 8/2008 | Wildman et al. |
| 7,597,122 B1 | 10/2009 | Smith |
| 7,605,704 B2 | 10/2009 | Munro et al. |
| 7,690,537 B2 | 4/2010 | Yates et al. |
| 7,815,075 B2 | 10/2010 | Simkins |
| 7,898,407 B2 | 3/2011 | Hufton et al. |
| 7,984,831 B2 | 7/2011 | Kanfer et al. |
| 7,988,020 B2 | 8/2011 | Shoham et al. |
| 8,038,034 B2 | 10/2011 | Pelfrey |
| 8,350,706 B2 | 1/2013 | Wegelin et al. |
| 8,556,128 B2 | 10/2013 | Harper |
| 8,558,701 B2 | 10/2013 | Wegelin et al. |
| 8,717,177 B2 | 5/2014 | Cartner |
| 8,844,766 B2 | 9/2014 | Zaima et al. |
| 2007/0229288 A1* | 10/2007 | Ogrin .................... G01F 11/006 340/573.1 |
| 2008/0103636 A1 | 5/2008 | Glenn et al. |
| 2010/0084486 A1 | 4/2010 | Kim |
| 2010/0094581 A1 | 4/2010 | Cagle |
| 2010/0117836 A1* | 5/2010 | Seyed Momen ......... G01S 1/70 340/573.1 |
| 2010/0188228 A1 | 7/2010 | Hyland |
| 2010/0238021 A1 | 9/2010 | Harris |
| 2011/0029353 A1 | 2/2011 | Sullivan |
| 2011/0093313 A1* | 4/2011 | LeBlond .......... G06Q 10/06398 705/7.42 |
| 2011/0169643 A1 | 7/2011 | Cartner |
| 2011/0182652 A1 | 7/2011 | Chung et al. |
| 2012/0218106 A1 | 8/2012 | Zaima et al. |
| 2012/0248140 A1 | 10/2012 | Iseri et al. |
| 2012/0274468 A1 | 11/2012 | Wegelin et al. |
| 2013/0262345 A1 | 10/2013 | Ciavarella et al. |
| 2013/0334248 A1 | 12/2013 | Iseri et al. |
| 2014/0081653 A1 | 3/2014 | Davis et al. |
| 2014/0103479 A1 | 4/2014 | Luc et al. |
| 2014/0253334 A1 | 9/2014 | Hanlin et al. |
| 2014/0266575 A1 | 9/2014 | Pelfrey |
| 2014/0266692 A1 | 9/2014 | Freedman et al. |
| 2015/0100335 A1* | 4/2015 | Englehard ........... G06F 19/3462 705/2 |
| 2016/0093194 A1* | 3/2016 | Herzog .................... G08B 3/10 340/573.1 |
| 2016/0140831 A1* | 5/2016 | Hermann ............. G08B 21/245 340/573.1 |

OTHER PUBLICATIONS

Biovigil Integrated Hand Hygiene System Video, 2013, video downloaded from http://www.biovigilsystems.com/products/video/ on Aug. 7, 2014 [CD-ROM].

Advantages™ Hand Hygiene Safety Real-time Technology for Safer Care, Hand Hygiene Demo Video, Versus Technology, Inc. 2014, video downloaded from http://www.versustech.com/rtls-solutions/hand-hygiene-compliance/ on Aug. 7, 2014, [CD-ROM].

Video Press Release of Proventix-Synapse Partnership, Proventix™ Partners with Synapse Wireless to Save Lives Two Alabama-based companies partner to fight healthcare acquired infections (HAIs), Jul. 12, 2010, video downloaded from http://www.youtube.com/watch?v=dZMqWxBvVKc on Aug. 7, 2014, [CD-ROM].

"About nGage," Proventix Systems 2012, downloaded from http://proventix.com/ngage on Aug. 5, 2014, 2 pages.

Sage Products, LLC ("Sage") Complaint against SwipeSense, Inc. ("SwipeSense" or "Defendant") Case: 1:13-cv-07910, dated Nov. 4, 2013, including Exhibits A-F, 54 pages.

Bonnie J. Schleder, John T. Brown, Patricia Moore, Charisma R. Trinidad, JohnJ. Vesely. Jr., "Increasing Hand Hygiene in a Medical/Surgical Intensive Care Unit," National Teaching Institute and Critical C:are Exposition to be held In Orlando, FL, May 19-May 24, 2012, 1 page.

"HyGreen: HyGreen and Hand Hygiene: How It Works," downloaded from http://www.hygreen.com/HandHygieneMonitor/How.asp on May 1, 2012, 4 pages.

Airista Solutions for Healthcare, "Unified Visibility Solutions (UVS)," 2010, 2 pages.

"Using a Real Time Location System to Reduce Hospital Acquired Infections," An Ekahau Solution Brief, 2011, 5 Pages.

Jessica Jeppsson, Emerging Technologies, Feb. 2011 Industrial Engineer-Emerging Technologies, downloaded from http://www.iienet2.org/IEMagazine/Details.aspx?id=23536 on May 1, 2012, 1 pages.

Video Press Release of Proventix-Synapse Partnership, Proventix™ Partners with Synapse Wireless to Save Lives Two Alabama-based companies partner to fight healthcare acquired infections (HAIs), Jul. 12, 2010, demo picture and article downloaded from http://www.prnewswire.com/news-releases/proventix-partners-with-synapse-wireless-to-save-lives-98141519.html on Jul. 28, 2014, 11 pages.

Biovigil Integrated Hand Hygiene System Video, 2013, demo pictures downloaded from http://www.biovigilsystems.com/products/video/ on Aug. 4, 2014, 31 pages.

"Dispensing Systems," Deb Group—commercial skin care products, downloaded from http://www.debgroup.com/us/products/dispensing-system on Aug. 5, 2014, 1 page.

Advantages™ Hand Hygiene Safety Real-time Technology for Safer Care, Versus Technology, Inc. 2014, downloaded from http://www.versustech.com/rtls-solutions/hand-hygiene-compliance/ on Aug. 5, 2014, 2 pages.

Advantages™ Hand Hygiene Safety Real-time Technology for Safer Care, Hand Hygiene Demo Video, Versus Technology, Inc. 2014, demo pictures downloaded from http://www.versustech.com/rtis-solutions/hand-hygiene-compliance/ on Aug. 5, 2014, 13 pages.

"Hand Hygiene Compliance Monitoring Solution," AiRISTA, LLC 2010-2013, downloaded from http://www.airista.com/applications/hand-hygiene-compliance.htm on Aug. 5, 2014, 2 pages.

"Hand hygiene compliance monitoring solution for infection control," Stanley Healthcare 2014, downloaded from http://www.stanleyhealthcare.com/solutions/health-systems/patient-safety/hand-hygiene-compliance-monitoring on Aug. 5, 2014, 2 pages.

Swipesense, How it Works, SwipeSense, Inc.2014, downloaded from https://www.swipesense.eom/#how_it_works, on Aug. 8, 2014, 7 pages.

* cited by examiner

Team Performance

| Team | Rate | % at Goal |
| --- | --- | --- |
| Blue | 11.2 | 67% |
| Pink | 9.6 | 42% |
| Orange | 9.6 | 50% |
| Purple | 9.5 | 38% |
| Yellow | 9.4 | 22% |

Support Center

- Help Center
- PCU Hand Hygiene Guidelines
- Requests, Suggestions, Questions
- Performance Manager Overview

| | | | | | |
| --- | --- | --- | --- | --- | --- |
| 3035 | C | 13.3 | 8.9 | 06/10/12 | 10.0 |
| 3036 | C | 10.7 | 6.8 | 06/12/12 | 10.0 |
| 3038 | M | 11.5 | 10.4 | 04/29/12 | 10.0 |
| 3039 | B | 10.7 | 6.0 | 06/13/12 | 6.0 |
| 3041 | 1 | 9.3 | 6.9 | 06/10/12 | 10.0 |
| 3042 | 2 | 7.7 | 8.5 | 06/13/12 | 10.0 |
| 3043 | M | 6.2 | 5.7 | 05/26/12 | 7.0 |
| 3044 | C | 10.2 | 13.2 | 06/13/12 | 10.0 |
| 3045 | B | 8.6 | 7.1 | 06/04/12 | 10.0 |
| 3046 | C | 12.4 | 4.9 | 06/09/12 | 10.0 |
| 3048 | M | 15.2 | 8.2 | 05/06/12 | 10.0 |
| 3050 | C | 11.1 | 10.5 | 06/12/12 | 10.0 |
| 3052 | 1 | 6.8 | 5.1 | 06/06/12 | 10.0 |
| 3054 | M | 4.8 | 4.9 | 05/18/12 | 10.0 |
| 3057 | 3 | 8.7 | 7.8 | 06/12/12 | 10.0 |
| 3058 | 4 | 6.0 | 4.4 | 06/13/12 | 10.0 |
| 3059 |   | 6.0 | 6.8 | 06/07/12 | 10.0 |
| 3066 | M | 9.8 | 8.1 | 05/24/12 | 10.0 |
| 3067 | C | 10.6 | 11.6 | 06/12/12 | 10.0 |
| 3068 | C | 13.4 | 10.3 | 06/11/12 | 10.0 |
| 3069 | C | 10.0 | 11.8 | 06/08/12 | 10.0 |
| 3070 | C | 15.2 | 9.0 | 06/12/12 | 10.0 |
| 3071 |   | 6.4 | 6.7 | 06/05/12 | 10.0 |

FIG. 4 (Cont.)

| To... | DEF.Test@Trial Hospital.org |
|---|---|
| Cc... | |
| Subject: | 7 weeks in a row above goal! |

ABC Personal Hand Hygiene System Update

Caregiver ID: 1022
Current Average Rate: 12.4
Goal Rate: 10.0
Unit Percentile: 85%

*Maintaining your average rate above your goal is a measure of clinical excellence!*

| Shift Date | Rate | Rate Average |
|---|---|---|
| 1/20/13 | 11.8 | 12.4 |
| 1/19/13 | 10.7 | 12.1 |
| 2/18/13 | 14.5 | 12.5 |
| 2/14/13 | 12.7 | 12.2 |
| 1/13/13 | 11.6 | 12.8 |
| 1/12/13 | 13.3 | 12.6 |

For more information click here.

FIG. 9

| To... | DEF.Test@Trial Hospital.org |
|---|---|
| Cc... | |
| Subject: | Performance slips can happen... |

ABC Personal Hand Hygiene System Update

Caregiver ID: 1022
Current Average Rate: 12.4
Goal Rate: 10.0
Unit Percentile: 85%

*Your Average Rate slipped below your goal. It can happen to any clinician. Just keep in mind the importance of fundamentals.*

| Shift Date | Rate | Rate Average |
|---|---|---|
| 2/20/13 | 8.8 | 8.4 |
| 2/19/13 | 7.7 | 9.1 |
| 2/18/13 | 6.5 | 9.5 |
| 2/14/13 | 5.7 | 10.2 |
| 2/13/13 | 11.6 | 10.8 |
| 2/12/13 | 13.3 | 10.6 |

For more information click here.

FIG. 10

| To... | DEF.Test@Trial Hospital.org |
| Cc... | |
| Subject: | Your valued feedback - was it ...? |

Momentum Hand Hygiene System - Your Valued Feedback

My rates continue to be below goal because ...

- I keep forgetting ——————————— (A)
- I have issues with the gel
- I have concerns about the tracking or accuracy ——— (B)
- I have issues with the personal dispenser ——— (C)
- something else ——— (D)

FIG. 11

(A) ABC

Performance Coach - Thank You
Thank you for your feedback
Your input helps us better support clinicians like you.

For related information:
- Tips for building clinical hand hygiene habits.
- Testimonials from clinicians.

(B) ABC Hand Hygiene

Performance Coach
Your Valued Feedback
My concern is:
- I question the accuracy.
- I have a lot of patients on contact precautions.
- I don't like the idea of being electronically tracked.
- I think other clinicians are gaming the system.

Something else:

⇒ Submit

Performance Coach

Your Valued Feedback

My concern is:
<u>I prefer using only soap and water.</u>
<u>I'm good with the wall mounted sanitizer dispensers.</u>
<u>I wear gloves a lot.</u>

Something else:

[→] Submit

---

D →

Performance Coach

Your Valued Feedback

Please share your thoughts:

[→] Submit

FIG. 11 (cont.)

| To... | DEF.Test@Trial Hospital.org |
| Cc... | |
| Subject: | "The minute you get away from fundamentals... |

ABC Personal Hand Hygiene System Update

Caregiver ID: 1022
Current Average Rate: 12.4
Goal Rate: 10.0
Unit Percentile: 85%

*Hand hygiene is an advanced clinical skill. It is a fundamental base of all other clinical practice.*

| Shift Date | Rate | Rate Average |
|---|---|---|
| 2/20/13 | 11.8 | 12.4 |
| 2/19/13 | 10.7 | 12.1 |
| 2/18/13 | 14.5 | 12.5 |
| 2/14/13 | 12.7 | 12.2 |
| 2/13/13 | 11.6 | 12.8 |
| 2/12/13 | 13.3 | 12.6 |

For more information click here.

FIG. 12A

| To... | DEF.Test@Trial Hospital.org |
| Cc... | |
| Subject: | Microbes are tough, but you must be tougher. |

ABC Personal Hand Hygiene System Update

Caregiver ID: 1022
Current Average Rate: 12.4
Goal Rate: 10.0
Unit Percentile: 85%

*Shoot for a rate of 8 per hour. You can do it!*

| Shift Date | Rate | Rate Average |
|---|---|---|
| 2/20/13 | 11.8 | 12.4 |
| 2/19/13 | 10.7 | 12.1 |
| 2/18/13 | 14.5 | 12.5 |
| 2/14/13 | 12.7 | 12.2 |
| 2/13/13 | 11.6 | 12.8 |
| 2/12/13 | 13.3 | 12.6 |

For more information click here.

FIG. 12B

| Step 1 – FIG. 9<br>Complement<br>Condition:<br>   at-goal or improving | Includes: Last 6 rates, complement<br>Examples:<br>   At-Goal now for 7 consecutive weeks<br>   New personal best rate average (or shift ave)<br>   Your average is almost to goal<br>   Near goal – within .5 of goal |
|---|---|//

⬇ Nothing good to say

| Step 2 – FIG. 10<br>Reminder<br>Condition: once each performance dip | Includes: Last 6 rates<br>Examples:<br>   Reminder – average goal rate short of goal<br>   Slipping – average goal just slipped |

⬇ Sent reminder last time

| Step 3 – FIG. 11<br>Feedback<br>Condition: once before each 4 Suggestions sets | Includes: Questions only. Some questions link to more specific question.<br>Examples:<br>   Your valued feedback – was it…? |

⬇ Feedback less than 4 suggestions ago

| Step 4 – FIGS. 12A, 12B<br>Suggestions<br>Rotate through 4 suggestions based on most recent Feedback | Includes: Last 6 rates, Hand Hygiene tip<br>Examples:<br>   Always sanitize before flushing a line<br>   Gloves are not a substitute for hand hygiene<br>   Focus on sanitizing in the patient nest<br>   Hands are contaminated over 10 times an hour |

FIG. 17

METHOD AND SYSTEM FOR ENSURING AND TRACKING HAND HYGIENE COMPLIANCE

This application claims the benefit of and is a continuation-in-part of U.S. application Ser. No. 14/029,746 filed on Sep. 17, 2013, which is a continuation-in-part of U.S. Provisional Application No. 61/702,013 filed on Sep. 17, 2012. Each of the above applications is incorporated herein by reference in their entirety.

TECHNICAL FIELD

The disclosure herein relates generally to a system and method for encouraging hand washing and for monitoring and determining compliance with hand washing requirements in healthcare settings.

BACKGROUND

Every year tens of thousands of people will die from infections they acquire while admitted as patient in a hospital. These hospital-acquired infections or nosocomial infections are unrelated to their initial hospital admission.

According to the CDC (Center for Disease Control & Prevention) in the United States, more than 50% of all nosocomial infections are transmitted due to improper hand washing by health care workers before and after each patient contact.

Health care workers have indicated that hand washing compliance is difficult because there is "not enough time and not enough conveniently located hand washing stations to wash hands as often as required." Compliance with hand washing guidelines is becoming worse and more difficult. Because of staff reductions, hospitals require healthcare workers to take care of an increasing number of patients during work shifts. Additionally, hospitals are seeing high transmission rates of antibiotic resistant bacteria and viruses, which requires stricter adherence to the CDC hand washing guidelines. Hospitals need products and services that boost and encourage hand washing, and methods to ensure and measure compliance.

BRIEF SUMMARY

The following presents a simplified summary of the disclosure in order to provide a basic understanding of some aspects. It is not intended to identify key or critical elements of the disclosure or to delineate the scope of the disclosure. The following summary merely presents some concepts of the disclosure in a simplified form as a prelude to the more detailed description provided below.

In one example, a computer-implemented method may include tracking the dispensing of a plurality hand hygiene dispensers having hand sanitizer and each hand hygiene dispenser being associated with an individual user. The method may include one or more of the following steps: determining by a processor dispensing rates of the plurality of hand hygiene dispensers for a plurality of predetermined time periods, identifying each of the plurality of the hand hygiene dispensers with an individual user, determining by a processor a predetermined number of highest dispensing rates out of the plurality of predetermined time periods and calculating an average dispensing rate based on the predetermined number of highest dispensing rates, displaying the dispensing rates of the plurality of hand hygiene dispensers, and notifying an individual user regarding the individual user's performance.

In another example, a system may include a plurality of hand hygiene dispensers, where each hand hygiene dispenser can include a housing configured to receive a container adapted to store hand sanitizer. The housing may include an input for detecting hand sanitizing events when hand sanitizer is dispensed from the container, and the input may be located within the housing. The housing may also include a memory for storing hand sanitizing events, and an accelerometer for recording motion information in memory and for determining whether the hand hygiene dispenser is in use. Each hand hygiene dispenser may be configured to communicate to a network via a low energy transmission protocol.

These and other aspects are discussed in greater detail throughout this disclosure, including the accompanying drawings.

BRIEF DESCRIPTION OF THE DRAWINGS

The present disclosure is illustrated by way of example and not limited in the accompanying Figures in which like reference numerals indicate similar elements and in which:

FIGS. 9-12B depict exemplary notifications for encouraging proper hand hygiene.

FIG. 17 depicts an example of a performance coach decision matrix.

DETAILED DESCRIPTION

Figure 1:
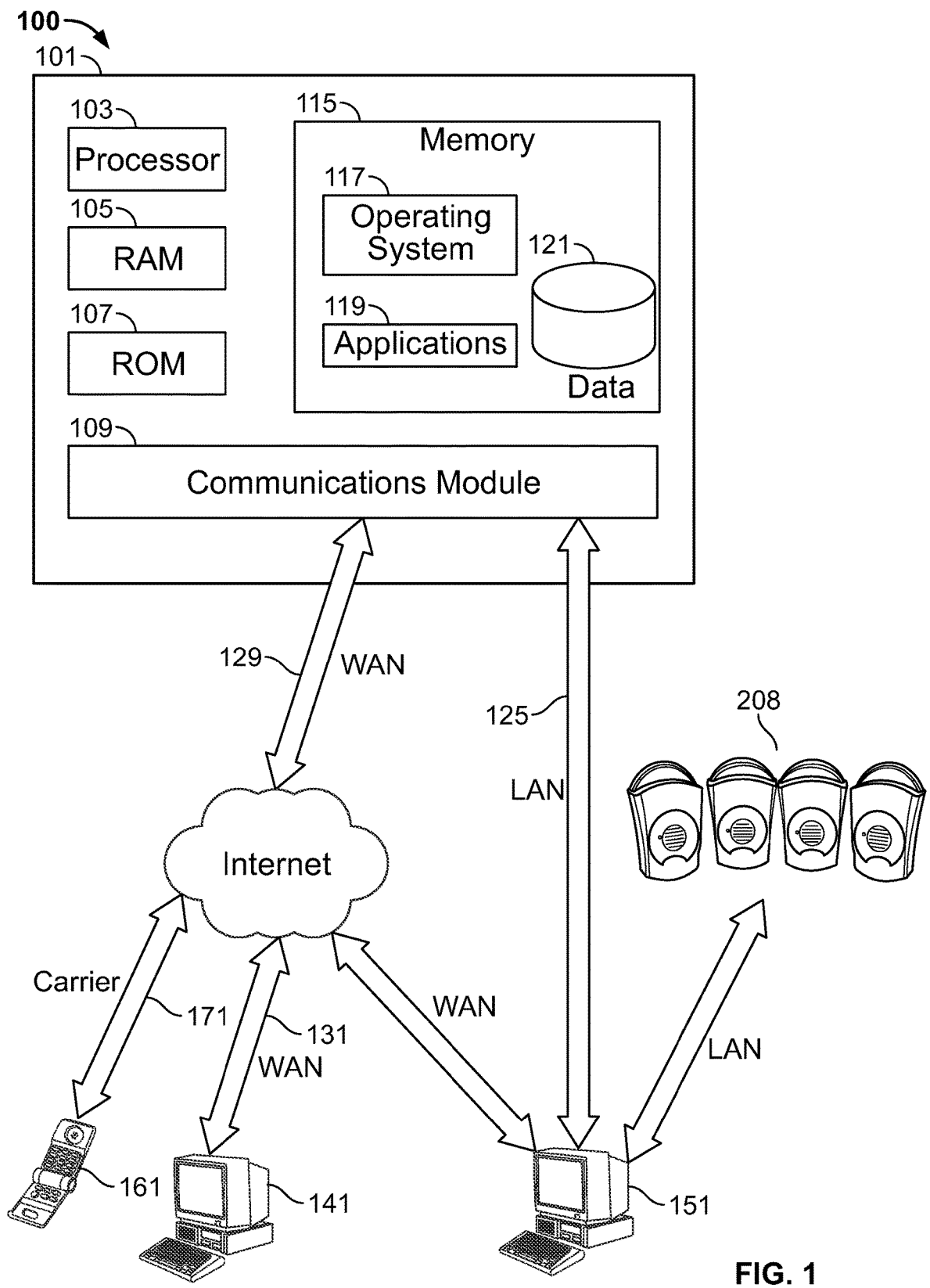
FIG. 1 shows an illustrative environment in which various aspects of the disclosure may be implemented.

In the following description of various example structures in accordance with this disclosure, reference is made to the accompanying drawings, which form a part hereof, and in which are shown by way of illustration of various structures in accordance with the disclosure. Additionally, it is to be understood that other specific arrangements of parts and structures may be utilized, and structural and functional modifications may be made without departing from the scope of the disclosure. Also, while the terms "top" and "bottom" and the like may be used in this specification to describe various example features and elements of the disclosure, these terms are used herein as a matter of convenience, e.g., based on the example orientations shown in the figures and/or the orientations in typical use. Nothing in this specification should be construed as requiring a specific three dimensional or spatial orientation of structures in order to fall within the scope of this disclosure. In the disclosure, various headings are used only for convenience purposes. These headings are not intended in any way limit the scope of the disclosure. Before discussing the aspects of the disclosure in greater detail, however, several examples of a network architecture and a data processing device that may be used in implementing various aspects of the disclosure will first be discussed.

I. Detailed Description of Example Network Architecture and Data Processing Device that May be Used to Example Methods for Ensuring Hand Hygiene Compliance Computing System FIG. 1 generally depicts a computing system environment 100 for implementing the hand hygiene monitoring methods described herein. The hand hygiene monitoring system can comprise a plurality of hand hygiene dispensers 208, a network, a computing device 101, branch computing devices 141 and 151, and one or more mobile devices 161. Each of the devices can be linked to the network by any known means. The hand hygiene dispensers 208 can be worn by health care workers or can be provided throughout a particular facility by any known means, such as a stand-alone units or wall-mounted units.

The computing system environment 100 is only one example of a suitable computing environment and is not intended to suggest any limitation as to the scope of use or functionality of the disclosure. The computing system environment 100 should not be interpreted as having any dependency or requirement relating to any one or combination of components shown in the illustrative computing system environment 100.

The exemplary embodiments disclosed herein are operational with numerous other general purpose or special purpose computing system environments or configurations. Examples of well known computing systems, environments, and/or configurations that may be suitable for use with the exemplary embodiments include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

With reference to FIG. 1, the computing system environment 100 may include a computing device 101 wherein the processes discussed herein may be implemented. The computing device 101 may have a processor 103 for controlling overall operation of the computing device 101 and its associated components, including RAM 105, ROM 107, communications module 109, and memory 115. Computing device 101 typically includes a variety of computer readable media. Computer readable media may be any available media that may be accessed by computing device 101 and include both volatile and nonvolatile media, removable and non-removable media. By way of example, and not limitation, computer readable media may comprise a combination of computer storage media and communication media.

Computer storage media include volatile and nonvolatile, removable and non-removable media implemented in any method or technology for storage of information such as computer readable instructions, data structures, program modules or other data. Computer storage media includes, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by computing device 101.

Communication media typically embodies computer readable instructions, data structures, program modules or other data in a modulated data signal such as a carrier wave or other transport mechanism and includes any information delivery media. A modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

Although not shown, RAM 105 may include one or more applications representing the application data stored in RAM memory 105 while the computing device is on and corresponding software applications (e.g., software tasks), are running on the computing device 101.

Communications module 109 may include a microphone, keypad, touch screen, bar code scanners, and/or stylus through which a user of computing device 101 may provide input, and may also include one or more of a speaker for providing audio output and a video display device for providing textual, audiovisual and/or graphical output.

Software may be stored within memory 115 and/or storage to provide instructions to processor 103 for enabling computing device 101 to perform various functions.

For example, memory 115 may store software used by the computing device 101, such as an operating system 117, application programs 119, and an associated database 121. Alternatively, some or all of the computer executable instructions for computing device 101 may be embodied in hardware or firmware (not shown). Database 121 may provide centralized storage.

Computing device 101 may operate in a networked environment supporting connections to one or more remote computing devices, such as branch terminals 141 and 151.

The branch computing devices 141 and 151 may be personal computing devices or servers that include many or all of the elements described above relative to the computing device 101. Branch computing device 161 may be a mobile device communicating over wireless carrier channel 171 or through a wireless LAN, WAN or a WiFi network.

The network connections depicted in FIG. 1 include a local area network (LAN) 125 and a wide area network (WAN) 129, but may also include other networks. When used in a LAN networking environment, computing device 101 is connected to the LAN 125 through a network interface or adapter in the communications module 109. When used in a WAN networking environment, the computing device 101 may include a modem in the communications module 109 or other means for establishing communications over the WAN 129, such as the Internet 131. It will be appreciated that the network connections shown are illustrative and other means of establishing a communications link between the computing devices may be used. The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Additionally, one or more application programs 119 used by the computing device 101, according to an illustrative embodiment, may include computer executable instructions for invoking user functionality related to communication including, for example, email, short message service (SMS), and voice input and speech recognition applications.

Exemplary embodiments discussed herein may include forms of computer-readable media. Computer-readable media include any available media that can be accessed by a computing device 101. Computer-readable media may comprise storage media and communication media. Storage media include volatile and nonvolatile, removable and non-removable media implemented in any method or technology for storage of information such as computer-readable instructions, object code, data structures, program modules, or other data. Communication media include any information delivery media and typically embody data in a modulated data signal such as a carrier wave or other transport mechanism.

Although not required, one of ordinary skill in the art will appreciate that various aspects described herein may be embodied as a method, a data processing system, or as a computer-readable medium storing computer-executable instructions. For example, a computer-readable medium storing instructions to cause a processor to perform steps of a method in accordance with aspects of the disclosure is contemplated. For example, aspects of the method steps disclosed herein may be executed on a processor on a computing device 101. Such a processor may execute computer-executable instructions stored on a computer-readable medium.

Figure 2:
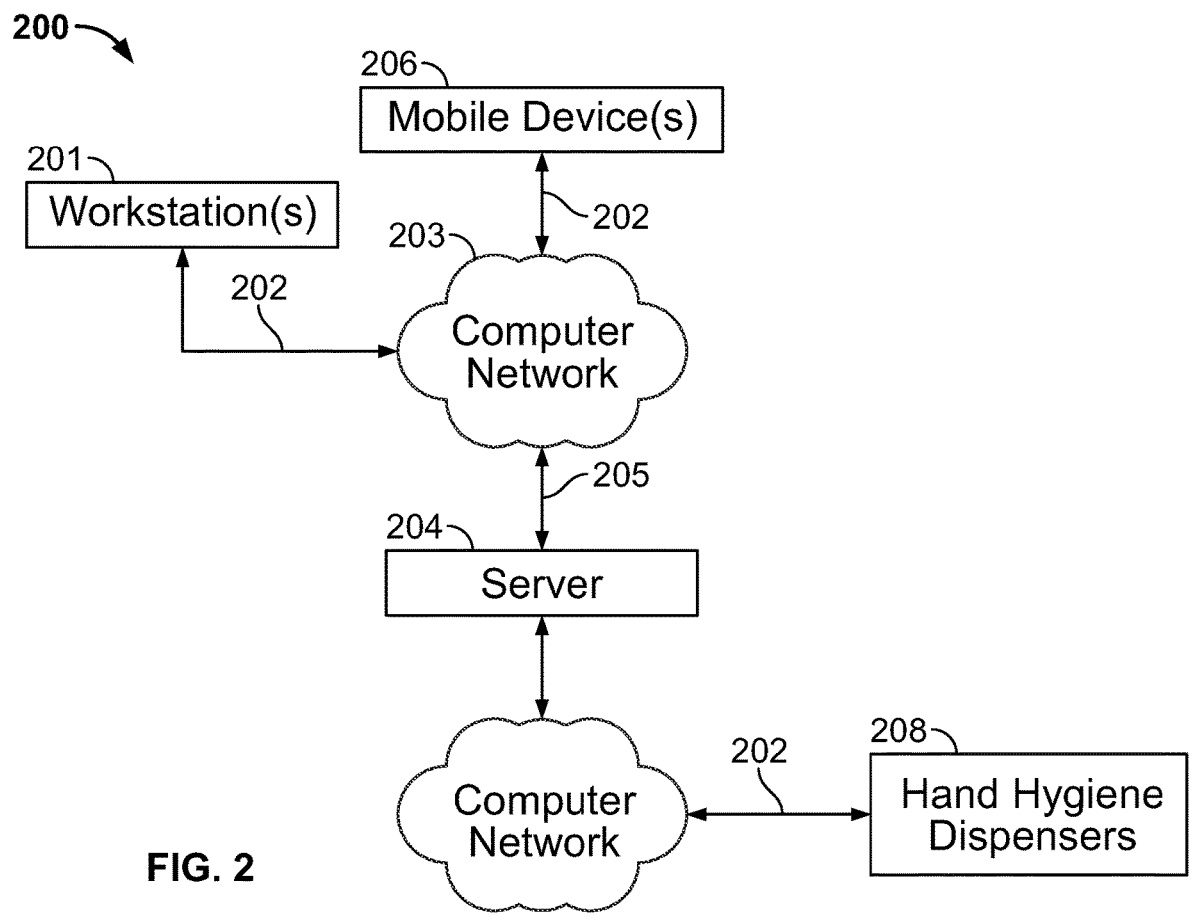
FIG. 2 is an illustrative diagram of workstations and servers that may be used to implement the processes and functions of certain aspects of the disclosure herein.

Referring to FIG. 2, an illustrative system 200 for implementing exemplary methods disclosed herein is shown. As illustrated, system 200 may include one or more workstations 201, mobile devices 206, and hand hygiene dispensers 208. Local or remote workstations 201, mobile devices 206, and hand hygiene dispensers 208 are connected by one of communications links 202 to computer network 203 that is linked via communications links 205 to server 204. In system 200, server 204 may be any suitable server, processor, computer, or data processing device, cloud, or combination of the same. Server 204 may be used to process hand hygiene data received from the dispensers 208.

Computer network 203 may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network (VPN), or any combination of any of the same. Communications links 202 and 205 may be any communications links suitable for communicating between workstations 201, mobile devices 206, and server 204, such as network links, dial-up links, wireless links, hard-wired links, etc. For example, the communications links 202 and 205 can be twisted pair wires, coaxial cable, fiber optics, radio waves (fixed or plug-in radio options), or other communication media. The communications links 202 and 205 can be made via the internet, Ethernet, Bluetooth, Wi-Fi, cell modems, or infrared. In one specific example, the communications links 202 and 205 can be made using a reduced power consumption type of communication or low-power radio signals, e.g., Bluetooth Low Energy (also referred to as "Bluetooth LE," "Bluetooth Smart," or "BLE"), Zigbee, and ISM. In one example, the ISM can be NFC. Nevertheless, any other known method of wireless transmission is contemplated for forming the above connections, including other highly efficient proprietary and custom protocols.

As understood by those skilled in the art, the system and steps that follow in the Figures may be implemented by one or more of the components in FIGS. 1 and 2 and/or other components, including other computing devices.

II. Detailed Description of Example Hand Hygiene Dispensers and Example Methods for Ensuring Hand Hygiene Compliance A computing system, which can be a calculation module, is configured to accept data from a plurality of personally worn devices attached to user's clothing or attached to a lanyard worn by the user to dispense hand washing agents. A series of algorithms in the computing system or the calculation module use the data to calculate and display various pieces of information relating to the user's hand hygiene behavior. This information may include: the user's hand hygiene rate of use, compliance to a set goal, reminders and remediation of lack of goal achievement, user location, total hand hygiene events, time in the clinical environment, various types of reports based on this information, etc. The information may also be used for reporting to management and regulatory/accreditation agencies. The computing system may also provide educational materials, facilitate communication between users and system administrators, and automated messaging to users, management and other interested parties. The computing system or the calculation module can reside in any location on the network can be implemented on any computing device of hand hygiene dispenser within the network. It is also contemplated that the computing system or calculation module can be a set of instructions stored on a computer usable medium and can be part of a computer readable program code embodied on the computer readable medium, such that the computer readable program code can be adapted to be executed by a processor to implement the methods and calculations pertaining to tracking hand hygiene performance.

In general, the hand hygiene monitoring system uses a set of algorithms in a computer readable medium that are executable by a processor to provide for automated hand hygiene compliance management and tracking and assists in achieving accountability to the user. The hand hygiene monitoring system can be implemented to help users be self-accountable to agreed-upon hand hygiene goals by providing direct and anonymous feedback to the user. However, in some exemplary embodiments, if the user continues to have poor hand hygiene performance then he/she may lose anonymity and must be accountable to a peer and/or manager. The hand hygiene monitoring system compares the user's average rate to a predetermined goal rate. If the average rate is less than the goal rate, the user receives notice, and the notice escalates with continued performance below the goal.

In some exemplary embodiments, each user is assigned a user ID number or alphanumeric ID sequence that is communicated to the user and by which users reference their anonymous hand hygiene data. In one example, when new users receive their dispensers, each dispenser can be associated with the particular user by the dispenser/user ID. For example, the dispenser could be provided with a barcode that can be scanned or the system can randomly or sequentially assign the dispenser/user ID once the user is provided with a dispenser.

In one example, the dispenser/user ID is only provided to the user. This can help the user's feel that management is not actively monitoring the user's hand hygiene habits and may help encourage effective participation in hand hygiene by users. For example, when new users are added, the software interface does not display the user ID or it may be represented as a series of asterisks. The user ID can be communicated to users by private email, text messaging, posted letter, or on peel-and reveal labels applied to their personal dispensers. In one example, to keep the hand hygiene data anonymous, there may be no way for management to list or review the user IDs associated with names. Users can find their hand hygiene data on computer monitors and reports by referencing their user ID or receive their hand hygiene data by email, text messaging, and the like. User IDs may be a minimum number of digits in order to be more easily remembered by users.

The number of discrete IDs can be maximized by segregating user groups by care unit and hospital or other organizational units. These multiple user groupings can be represented in the database as codes combined with the user ID the user sees. For example, there may be a hospital code, e.g., GENH, a care unit code, e.g., SICU, and a user ID, e.g., 1234 to be internally combined in the database, e.g., GENH_SICU_1234. This method accommodates a virtually unlimited number of user IDs as users will not physically see a duplicate user ID at other facilities or locations.

Personal Hand Hygiene Dispensers

Figure 3:
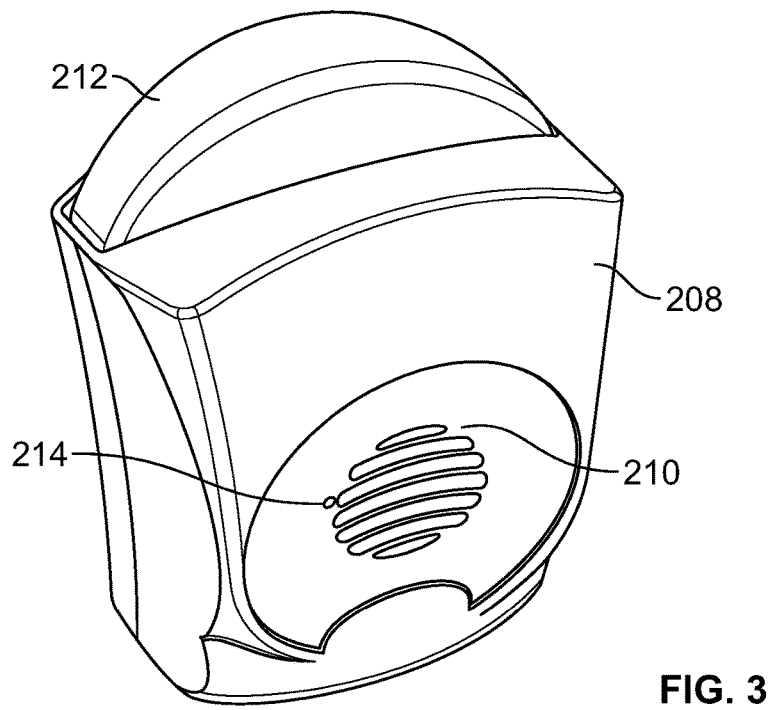
FIG. 3 depicts a front, left perspective view of an exemplary embodiment of a personal hand sanitizer dispenser.
Figure 3B:
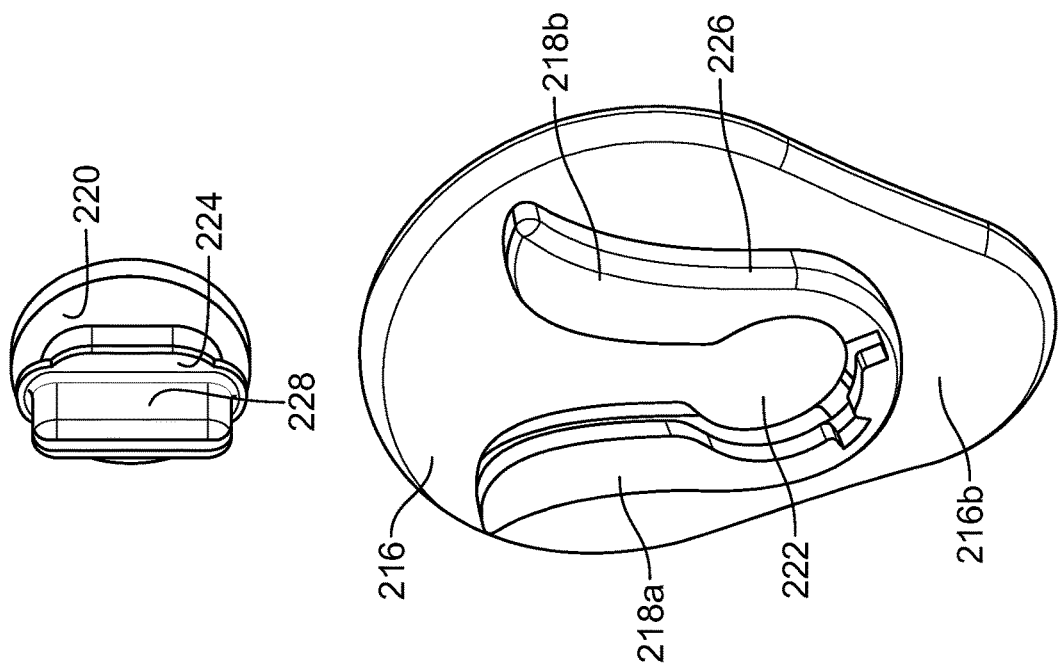
FIG. 3B depicts another perspective view of the exemplary embodiment in accordance with FIG. 3A.
Figure 3A:
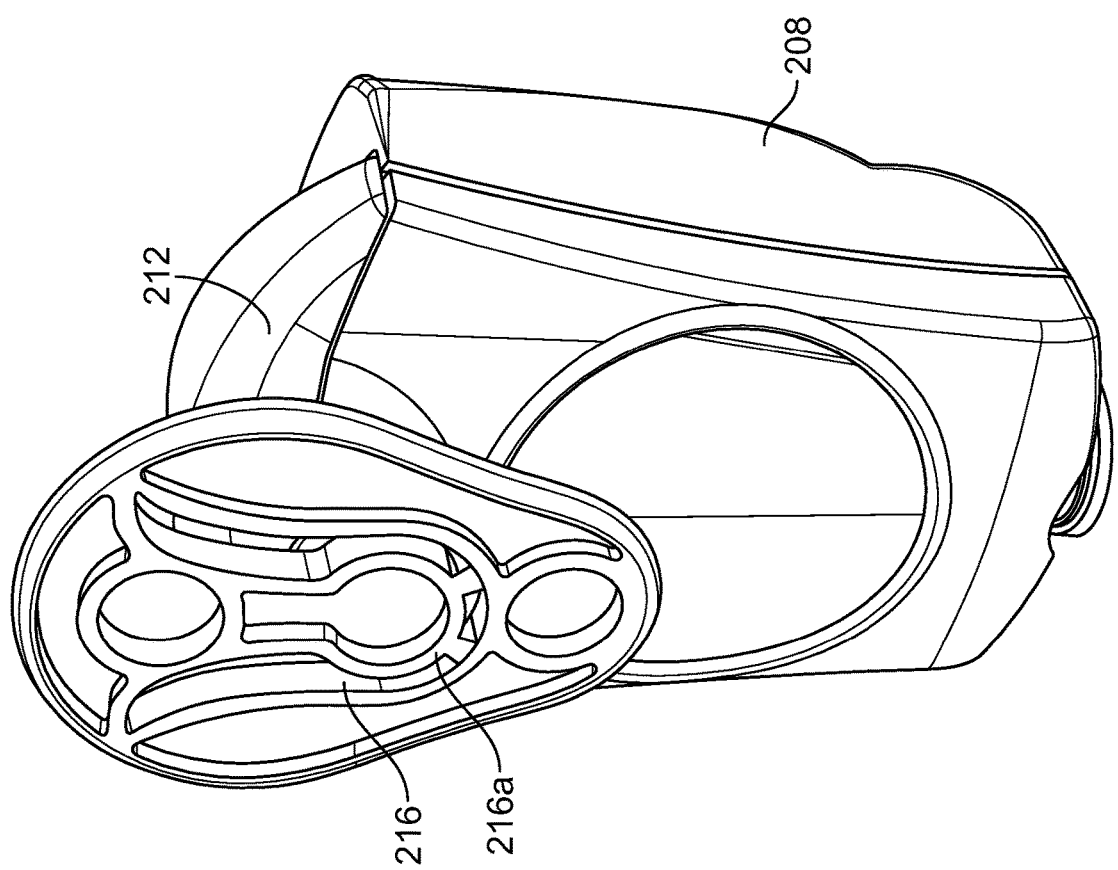
FIG. 3A depicts a perspective view of another exemplary embodiment of a personal hand sanitizer dispenser.

As depicted in FIG. 3, the personal hand hygiene dispensers 208 may comprise a reservoir 212 for hand sanitizer, an actuator 210 for dispensing hand sanitizer, an attachment mechanism (not shown) for attaching the dispenser 208 to the health care worker's clothing or lanyard, a RF, IR, or other known type of wireless transmitter, memory circuit, and a light indicator 214 for the actuator 210. Additionally, the hand hygiene dispensers 208 can include a processor, RAM, ROM, and a memory for storage to provide instructions to the processor for enabling the hand hygiene dispensers 208 to perform various functions. In yet another example, the dispenser 208 may also include a display screen for displaying performance data, such as the user's average dispensing rate, to the user.

The reservoir 212 can be a refillable reservoir or can be implemented as a replaceable cartridge. The contents of the cartridge are squeezed through an opening in the back of the dispenser (not shown) to dispense hand sanitizer while the actuator 210 is pressed simultaneously to send a signal via a transmitter to indicate to the server that a hand hygiene event has occurred. It is contemplated that the actuator can both dispense the hand sanitizer from the dispenser 208 and activate the transmitter to send the signal indicating that a hand hygiene event has occurred. In one embodiment, the actuator 210 triggers a switch attached to or on the memory circuit in the dispenser that records the event to be downloaded to a computer, for example, when the actuator is synced. The actuation may be associated with a time interval that is stored in the memory circuit and represents the time and date of each activation.

In another example, the dispensing action can be stored on the dispenser computer for downloading at a later time. This minimizes the use of power by the personal dispenser 208. In one example, the transmitter can be programmed to look for a signal periodically (e.g. once an hour) and download dispensing or other performance data at that time. In another exemplary embodiment, the plurality of personal dispensers 208 may individually be placed in a designated area at the end of the user work day, and the data can be transmitted (e.g. via WiFi) to the server. Other known techniques for transferring the data from the dispensers 208 to the server are also contemplated.

The personal dispenser 208 may be outfitted with a sensor (not shown) to detect the amount of dispensing fluid located in the reservoir 212, and the sensor or an additional sensor can also be configured to detect when the reservoir 212 of the hand sanitizer is changed by the user or otherwise in the personal dispenser 208. The sensor or additional sensors can also be configured to detect whether the user is using an appropriate amount of hand sanitizing solution.

In another embodiment not shown, the personal dispenser 208 can also be outfitted with firmware programming and an electronic display to display the user's immediate hand hygiene rate or number of uses within a given time period. The time period for the rate or number of uses can be based on shift or work periods calculated by the firmware (motion detection since a period of inactivity) or downloaded from a server. This display can be provided to help the user stay on track with reaching a goal hand hygiene rate.

The user can carry the dispenser by attaching the dispenser 208 to his/her clothing via any known attachment mechanism. One example of an attachment mechanism 216 is provided in FIGS. 3A-3D. The attachment mechanism 216 can help attach the dispenser 208 to the user's clothing. The attachment mechanism 216 can attach to the user's clothing by use of magnets. Two magnets can be located on the first side 216a of the attachment mechanism 216 for securing the attachment mechanism 216 to the user's clothing. In particular, a corresponding bar (not shown) with magnets can be placed on the opposite side of the user's clothing, and the bar can be aligned with the first side 216a of the attachment mechanism 216 to magnetically secure the first side 216a of the attachment mechanism 216 to the user's clothing.

On the second side 216b, the attachment mechanism 216 can be formed with two slots 218a, 218b formed from a protruding component 226 of the attachment mechanism 216. The slots 218a, 218b can be configured to receive a circular disk-shaped member 220 therein to align the disk-shaped member 220 with a corresponding circular recess 222 also formed by the protruding component 226.

The disk-shaped member 220 has an oblong-shaped cam 224. The cam 224 aids in securing the attachment mechanism 216 to the dispenser 208 by locking the disk-shaped member 220 between the recess 222 and the protruding component 226. The disk-shaped member 220 is also provided with a projection 228, which is configured to snap into a corresponding slot 232 on the dispenser housing 230. The projection 228 can be formed by two male flexible elements 228a, 228b that are configured to securely fit within the corresponding slot 232 via a snap-fit connection.

To attach the dispenser housing 230 to the attachment mechanism 216, the projection 228 is aligned with the slot 232. This allows the projection 228 two flexible elements 228a, 228b to snap into a locking engagement with the slot 232 on the dispenser housing 230.

The disk-shaped member 220 and cam 224 can then be aligned with the two slots 218a, 218b formed in the protruding component 226 of the attachment mechanism 216 until the disk-shaped member 220 is held within the corresponding circular recess 222. Once the disk-shaped member 220 is held within the corresponding circular recess 222, the user can then twist the disk-shaped member 220 until the dispenser 208 is upright such that the cam 224 holds the disk-shaped member in the recess 222 by locking the disk-shaped member 220 between the recess 222 and the protruding component 226.

The user can then attach the dispenser 208 to his/her clothing by placing the bar with magnets on the inside of his/her clothing and then securing the first side 216a of the attachment mechanism 216 to the outside of his/her clothing. In this way, the bar is aligned with the first side 216a of the attachment mechanism 216 to magnetically secure the first side 216a of the attachment mechanism 216 to the user's clothing.

The personal dispenser can also be provided with a switch and dispensing mechanism, for example, a pump or pressurized container that would dispense a predetermined amount of hand sanitizer solution each time the user activates the switch in order to ensure that an appropriate amount of hand sanitizer is used. In this way, the user will rub an appropriate amount of hand sanitizer on his/her hands. This also makes it difficult for the user to avoid using the requisite amount, and ultimately this could encourage use and could discourage cheating or users from using too small of amounts of hand sanitizer.

The exemplary embodiments discussed above describe a personal dispenser that the user can wear on his/her clothing, carried by the user in the user's clothing or worn by the user on a lanyard, etc. A personally worn dispenser can always be available, especially around the patient when it is needed. However, it is also contemplated that the dispenser can be stationary in a given treatment area and can be, for example, wall mounted or mounted on a stand.

Methods of Operation

The dispensers 208 can be provided to a plurality of users for use during the users' work shifts. Each individual dispenser 208 is uniquely identified with a particular user such that the user's dispensing rate can be tracked and logged. The dispenser electronics are uniquely identifiable by a "tag ID" which can be stored in the dispenser's ROM. This ID is a code that is unique to a specific dispenser and can be transmitted along with other data when the actuator 210 is activated. This ID can be an RFID. The tag ID is then associated with a user code and can be assigned to a user in the dispenser configuration software. The user code can be assigned such that only the user knows their particular user code so that the dispenser tracking can remain anonymous as discussed above. The user code is used to identify any data calculated for an associated user and displayed by the system.

During use, the user presses the actuator 210 and squeezes the cartridge/reservoir to dispense hand sanitizer from the reservoir 212 onto his/her hands. The actuator 210 also triggers the transmitter within the dispenser housing and the light indicator 214 or other audible or tactile mechanism to notify the user that a signal has been transmitted. The transmitter communicates with the network to record that a hand hygiene event has occurred by sending a unique identifier along with a time and date stamp through the network to a data collector.

The transmitter can communicate wirelessly over the network, e.g., Wi-Fi, to a central server. Additionally the transmitter can communicate with one or more data collectors that are connected via wire or wirelessly to the network. The transmitter can indicate to the server the dispenser's unique ID, the time the dispenser is within a given area, the time of the dispensing action, the location of the dispenser, and the particular dispenser that is used. The time of the activation could also be established by the server based on the real-time receipt of a communication from the dispenser triggered by the activation of the dispenser. This can then be stored in a server located in a healthcare facility or can be sent to an outside server or cloud. The data is then analyzed as discussed herein to determine whether the user is meeting hand hygiene rate goals.

In one exemplary embodiment, during use, the personal dispenser is configured to sense the amount dispensing fluid located in the reservoir 212 and can notify the user when the dispenser 208 needs to be refilled. The dispenser 208 can also notify the network via the transmitter when the reservoir 212 of hand sanitizer has been changed for tracking and servicing purposes. The dispenser 208 can also track whether the user is using an appropriate amount of hand sanitizing solution and notify the network if the appropriate amount of hand sanitizing solution is not used. The dispensing amount can be monitored by recording the number of dispenser activations and comparing the number of activations with the amount of hand sanitizer in the reservoir to determine if an appropriate amount of sanitizer is being used. Additionally, another sensor can be provided to detect battery life of the dispenser, which can be displayed to the user on the dispenser or sent to the user via text, email, dispenser display, kiosk, or any other known method of communicating with the user.

In alternative exemplary embodiments, during a predetermined time period or shift of the user, an electronic screen displays the user's immediate real-time and/or historical hand hygiene rate, which can be viewed by the user at any time during the shift to assist the user with staying on track to reach a goal rate. The personal dispenser electronics can have capabilities to sense activation of the actuator then calculate and display the rate on the dispenser. The dispensing rate can be calculated by the server and then delivered to the dispenser display or the dispenser can internally calculate the dispensing rate. The display could be LED, LCD, or any other known displays in the art. In addition, the real-time hand hygiene rate can also be displayed on an external display to provide immediate confirmation to users that their dispensers are transmitting data properly. Other methods of notifying the user of the dispensing rate, e.g. text, email, social media, and the like.

When displaying the hand hygiene rate to the user on the display, it may be desirable to display an accurate real time hand hygiene rate. For example, if the user's goal rate is 10 uses/hour, the system can collect the current activations of the dispenser and divide by 6 minute increments and convert to hours by multiplying by 60. When the user first activates the dispenser to dispense alcohol gel or sanitizer the rate would be: 1/6 minutes×60 minutes/hour=10 uses/hour. This would continue for 6 minutes. After 6 minutes the program would advance and the denominator would change to 12 minutes. Therefore, if the user did not perform any more hand cleansings the rate would be 1/12 minutes×60 minutes/hour=5 uses/hour. If the user performed 2 more cleansings during this period the rate would be calculated as 3/12 minutes×60 minutes/hour=15 uses/hour. Using the six minute increments would smooth the values that would be displayed.

Determining Compliance and Hand Hygiene Rates

The hourly hand hygiene rate can be calculated by taking the number of dispenser activations divided by the working time on the shift in hours and minutes. For example, hand hygiene rate=100 dispenser activations/10 hours worked on the shift=10 dispenser activations/hour. For example, the rate for 75 dispenser activations over 8 hours and 35 minutes of working time is calculated as $$\frac{75 \text{ activations}}{(8 \text{ hours} \times 60 \text{ min}) + 35 \text{ min}} \times \frac{60 \text{ min}}{1 \text{ hr}} = 8.7 \text{ activations/hour}$$

The working time used to calculate the hand hygiene rate can be established by the electronically detected time spent by users within a discrete clinical area. The working time may or may not account for the user leaving the discrete clinical area for breaks, lunch, or to work in other areas. Electronically detected (i.e. radio frequency, infrared, ultrasound, others) duration can be established by one or more of the following:
(1) calculating the time between electronically detected entry into a discrete clinical area and comparing that time to the time of electronically detected exit out of the discrete area,
(2) periodic electronic detection of electronics carried by the user within the discrete area every N seconds/minutes (for example, personal dispenser electronics send out an RF signal every 15 seconds to a data collector that has a range that approximates the area of the care unit),
(3) optionally using electronic motion detection in the electronics carried by the user to eliminate time periods when the electronics are not active on a user, or
(4) downloading data from an integrated employee time keeping system or database.

In another exemplary embodiment, the hand hygiene rate can be normalized. For example, the mean of the best three of the last six shift rates can be used to determine the user's hand hygiene performance. This accounts for shifts that are low due to factors beyond the user's control, for example, taking care of patients that are on isolation precautions or taking care of patients with *C. difficile* infections which require soap and water hand hygiene. Also isolating the previous six shifts keeps the rate recent and relevant as this typically covers a one and one half to two week period. Using the mean also factors in low or high performance.

In another exemplary embodiment, the hand hygiene rate of the unit or group of workers can be normalized by taking the median rate of all of the workers in the particular unit or group. Taking the median rates of the unit or group can account for the outliers at the low end or high end of the hand hygiene rate range.

In another embodiment, the monitoring system can be configured to determine whether the user attempts to "game" or cheat the system. For example, the system can review whether the user used the dispenser several times during a short duration during the shift, such as at the end of the shift when the user may want to "catch up" their goal rate. In another example, a run chart type system can be used. A run chart can evaluate the data and the likelihood that the data is "in control." In this example, the system can be configured to detect trends and out-of-control conditions with data over time.

In another example, the system could also review hand hygiene rates to determine appropriate patterns associated with hand hygiene. This could be accomplished by correlating the events with known work patterns to account for types of patients being seen, treatments, other activities, etc. Moreover, the system could communicate and correlate with other systems, such as the time clock system to correlate times with work patterns, for example, and may discount time for lunch periods, breaks, etc.

The shift data is evaluated by calculating the time between consecutive actuator activations. Each data point is compared to the mean of all the points combined. If X consecutive points fall below the mean, it indicates an anomaly in the way the user is using his/her dispenser. This user may be "flagged" and additional shift data can be analyzed to look for a pattern of "cheating." The X consecutive points and number of shifts to review are under evaluation. For example, in a typical control chart if 9 consecutive points are below the mean the system is "out of control." If this pattern is during a particular part of the shift, for example, near the end, it may also be flagged for cheating.

In another exemplary embodiment, the system can track the movement of the dispenser to see whether the user is cheating by detecting the time between dispenser movements. For example, if a user leaves the dispenser on a counter and only picks it up infrequently to use it could appear that the rate is high, but because of the minimal movement of the sensor this can be detected.

In another exemplary embodiment, the hand hygiene rate can be assigned to a clinical date to coincide with work shifts that run from approximately 7 AM to 7 AM the next day so night shift users don't have to see their shift rate broken up over two dates. The electronic time stamp records from the dispenser transmitter are used to set the duration based on when the shift started approximately. If a user starts a day shift before the 7 AM shift change or stays after a 7 AM night shift end, the records are joined with the actual shift date worked.

In another exemplary embodiment, the system can base coaching tips based on users' hand hygiene data compared to established champion or exemplary hand hygiene data patterns based on position, setting, and duties. Champion or exemplary data pattern templates are established by observation and personal dispenser data collection for a number of champions for a given position and setting. The patterns can represent common segments of duties performed. The timing between appropriate hand hygiene events can be approximated into templates.

Ongoing user data from similar positions and settings can be compared to these patterns. A series of pattern alignments can signify exemplary hand hygiene performance prompting compliments and encouragement in communications such as emails or text messages. A lack of alignment could potentially elicit further review of the pattern misalignments to generate intelligent suggestions to promote specific hand hygiene behaviors. The data could also be combined with other electronic data such as motion detection or radio/infrared/ultrasound detection of entering/exiting discrete areas. For example, the data pattern could indicate a doctor is doing rounds on an ICU and failing to use the personal dispenser when approaching the next patient. An email could be sent making the suggestion the doctor works harder to use the dispenser when approaching patients. Another pattern example is an ICU RN changing a catheter collection bag where there should be a series of hand hygiene events before and after donning gloves. In this scenario the system can be configured to send an appropriate reminder message to the user.

Providing User Feedback

As discussed above, the system can provide for user accountability in compliance with hand hygiene. In an exemplary embodiment, a performance manager is intended to help the user be self-accountable to agreed-upon hand hygiene goals. However, if the user continues to exhibit poor performance then he/she may lose anonymity and must be accountable to a peer and/or manager. The system can be configured to allow for flexibility in setting up the accountability structure and other methods of holding the users accountable are contemplated.

In one exemplary embodiment, the performance manager can be configured to send a notification to the user regarding the user's hand hygiene performance. In one example, the performance manager can compare the user's average rate to a predetermined goal rate over three (more or less) shifts. If the average rate is less than the goal rate, the user may receive a warning and the warning level escalates with continued performance below the goal. This warning can be sent to the user via text, email, dispenser display, kiosk, or any other known method of communicating with the user.

Table 1 shows an exemplary embodiment of a method of providing user feedback and ensuring user feedback. As shown below, the performance manager has various levels of user performance. However, the number of levels and the actions taken at each level may be modifiable by the system administrator within certain limits. That is, the administrator may be able to select the number of levels and the action for each level from a menu when initiating the system. Depending on the level of performance, the system can be configured to notify the user of good performance, average performance, below average performance or require the user to take various actions to help encourage the user to comply with the facility's hand washing requirements. In one example, the goal hand hygiene performance rates can be based on published data from the CDC or other public health institutions.

In another example, the goal hand hygiene rates can be based on work patterns for varied clinical roles. For example, a health care worker in an ER will have different duties and activity level than a health care worker in a doctor's office or intensive care unit. The work patterns can be analyzed with predetermined templates for each health care worker type e.g., the appropriate level of hand hygiene events for the particular health care worker type. For example, the health care worker's hand hygiene event data can be compared to the templates for the appropriate clinicians to automatically make suggestions on how to improve appropriate clinical hand hygiene performance. These suggestions can be made in the form of text, icons, or audible reminders on the personal hygiene dispensers, in emails or texts to the users or other electronic methods. The templates can be created by calculating ideal hand hygiene rates for each worker type or from historical data from the particular worker type.

TABLE 1

| Performance Level | Description | Action and/or purpose |
| --- | --- | --- |
| Level 0 | Average rate is in compliance with the goal rate | No action taken or system sends notification that user is in compliance with the goal rate. A notification could be sent to the user to indicate the user has illustrated exemplary performance of hand hygiene. |
| Level 1 | Average rate (see above) is less than goal rate (minimum of six shifts before the system activates) | Warns the user that their rate has been below the goal rate. The system can be configured to send the warning via e-mail, text, a touch screen "kiosk" on the unit to access the information or any other known method. For this and all subsequent levels the user then has three shifts to get their average up to the goal rate, however, if they achieve the goal rate for a shift, but their average is still below goal, they earn an additional shift to get their average up to the goal. |
| Level 2 | Average rate is less than goal for three additional shifts, six total shifts. | The user is prompted to go to the web based "Issue Handler," a guide to help the user explore issues that may be keeping him/her from achieving the goal rate. They must respond that they have consulted this tool. The user then has three shifts to get their average up to the goal rate. |
| Level 3 | Average rate is less than goal for three additional shifts, nine total. | The user must review an instruction, audio file, a web video, etc. and pass a quiz on the information. The content can be placed on a web based-hand hygiene system/server. |

TABLE 1-continued

| Performance Level | Description | Action and/or purpose |
| --- | --- | --- |
| Level 4 | Average rate is less than goal for three additional shifts, twelve total. | The user must set up a meeting with a peer counselor or manager to discuss his/her hand hygiene performance and develop an improvement plan. This can be the first time the user has lost anonymity in the compliance system. |
| Level 5 | Average rate is less than goal for three additional shifts, fifteen total. | At this level the user may be required to meet with a manager, infection preventionist, etc. or may receive a formal reprimand. The consequences are decided upon prior to implementation of the system and can be ultimately decided by the administration of a particular facility. |

In another exemplary embodiment, the performance manager can send emails or surveys to low-performing users to elicit their response to questions to identify behavior change barriers. The behavior change barriers are based on user objections from past experience or are designed to help pinpoint components of behavior-change models such as Health Belief Model, Theory of Reasoned Action, Theory of Planned Behavior, Self-Efficacy, and the Transtheoretic Model. Based on the user's answer, the system can direct users to information that addresses their specific objections. All answers are stored in a database to be used to analyze the barriers for a given user, care unit, hospital, or region.

In one exemplary embodiment, a performance coach sends regular communications to users to encourage improvements or to sustain good performance. Exemplary communications are depicted in FIGS. 9-12B. Each correspondence may be in the form of email, printed report, text message, or other method of correspondence. These communications may be sent after each recorded shift or day of hand hygiene data or after a regular sequence of days or shifts, for example after three shifts. As depicted in FIGS. 9, 10, and 12, these communications may include a summary report of the user's hand hygiene performance for the most recent shifts or days of hand hygiene recorded. Based on the most recent performance, the correspondence can be based on a decision matrix.

In one example, the decision matrix can be a set of prioritized steps. The steps can initiate a correspondence to recognize conditions of performance over time. For example, a top priority may be to first recognize any form of good performance such as consistent performance above the goal rate, a recent shift performed at or above a goal rate, or an improved performance above the user's average even if below a predetermined goal. The next level of priority may be a reminder that performance is below a goal that can be sent only once initially and then once per performance dip.

In one exemplary embodiment, as illustrated in FIG. 11, one of the subsequent performance coach steps can be to provide a periodic communication that elicits a response to a question with multiple choice answers based on common barriers to successful hand hygiene adherence. A short question with a limited number of multi-choice answers may be asked in an email and one or more of the answer selections may branch to an additional question with additional multiple choice answers from a web page. Selection of those answers may also branch to another question and set of answers in another web page. Ad-hoc answers can also be entered in text boxes. All answers are recorded and assigned to the user in a database to be used to categorize future tips or suggestions aimed at addressing the common barriers to proper hand hygiene. Ad-hoc text responses are stored for later review and may be used to expand the question and answer set.

As shown in FIGS. 12A and 12B, subsequent prioritized steps in the decision matrix may be to send a series of common tips, quotes, or motivational text. These may be categorized by recent responses to the multiple choice questions aimed at identifying common hand hygiene barriers. These categorized tips, quotes, or suggestions may be selected from within a pool randomly or stepped through sequentially as to avoid repeats. These intelligent tips, quotes, or suggestions may also be placed in the subject line of an email or sent as text messages. User responses to the questions may also be stored to be used to tailor the content of educational online courseware the user may be asked by email or text to perform. The user responses may also be used to initiate corresponding related real-time reminders using the audio, light, or tactile or other output devices. An example of the performance coach decision matrix is shown in FIG. 17.

In one exemplary embodiment, the personal dispenser light, audible, or tactile electronic circuit can be used to help train the user to new hand hygiene behaviors. This reminder system can use all available data to establish activation patterns of the reminder by light, audible, or tactile circuit. The circuit could recognize the personal dispenser has entered a patient care area and then activate the reminder every N minutes. N would correspond to the goal rate for that user based on position and setting, for example, an ICU RN with a goal rate of 8 initiates a reminder every 5 minutes when in the immediate patient surrounding. The timing of the reminder can also be based on established champion hand hygiene data patterns based on position, setting, and duties. The use of the reminder can also be based on user answers to performance coach questions.

Displaying of Hand Hygiene Performance Feedback

There are a number of ways that hand hygiene compliance data can be displayed to the users and management for a particular facility or set of facilities. FIGS. 4-8 depict a few exemplary displays for providing feedback.

Figure 4:
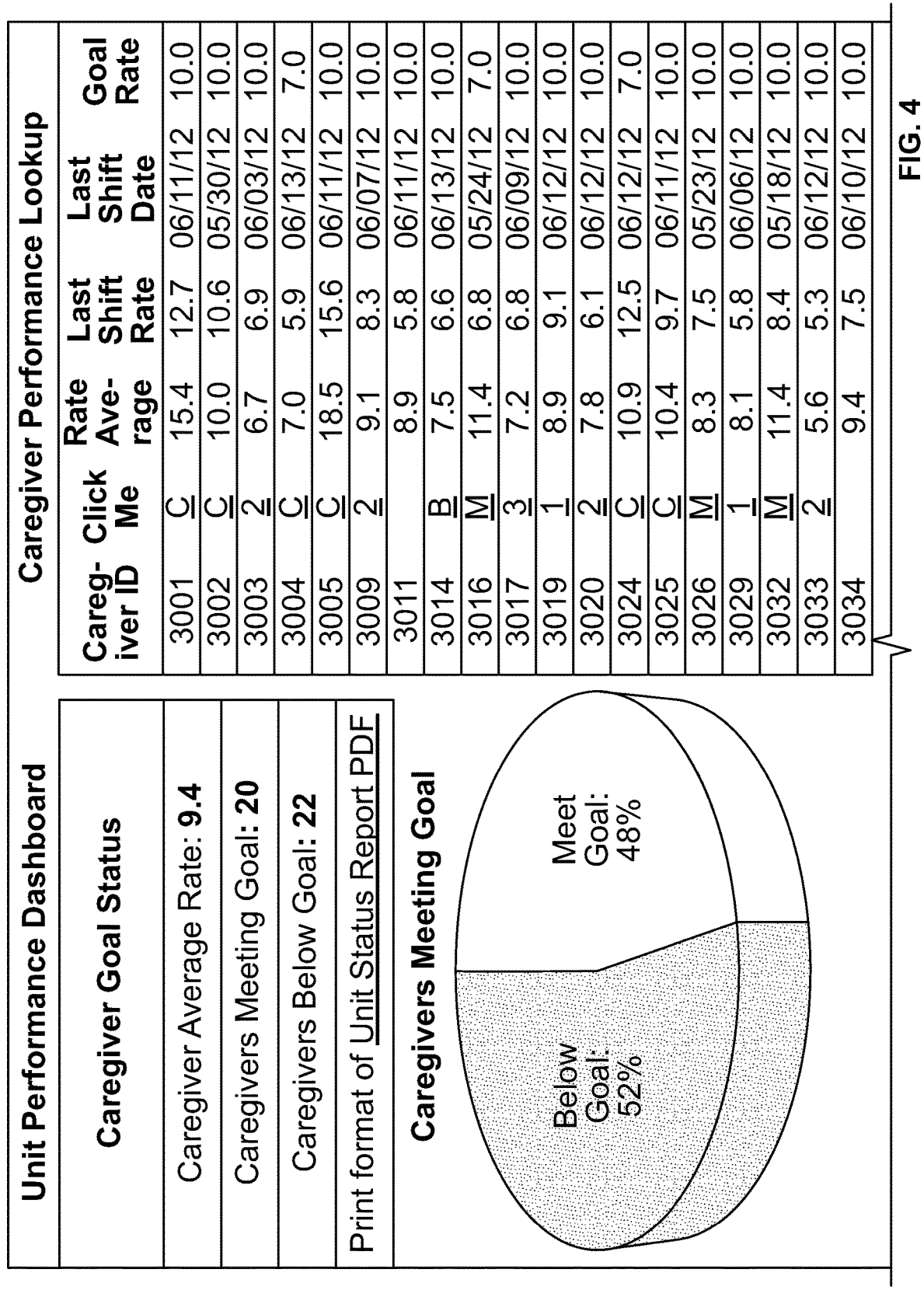
FIGS. 4-8 depict exemplary displays for displaying hand hygiene and related data.
Figure 5:
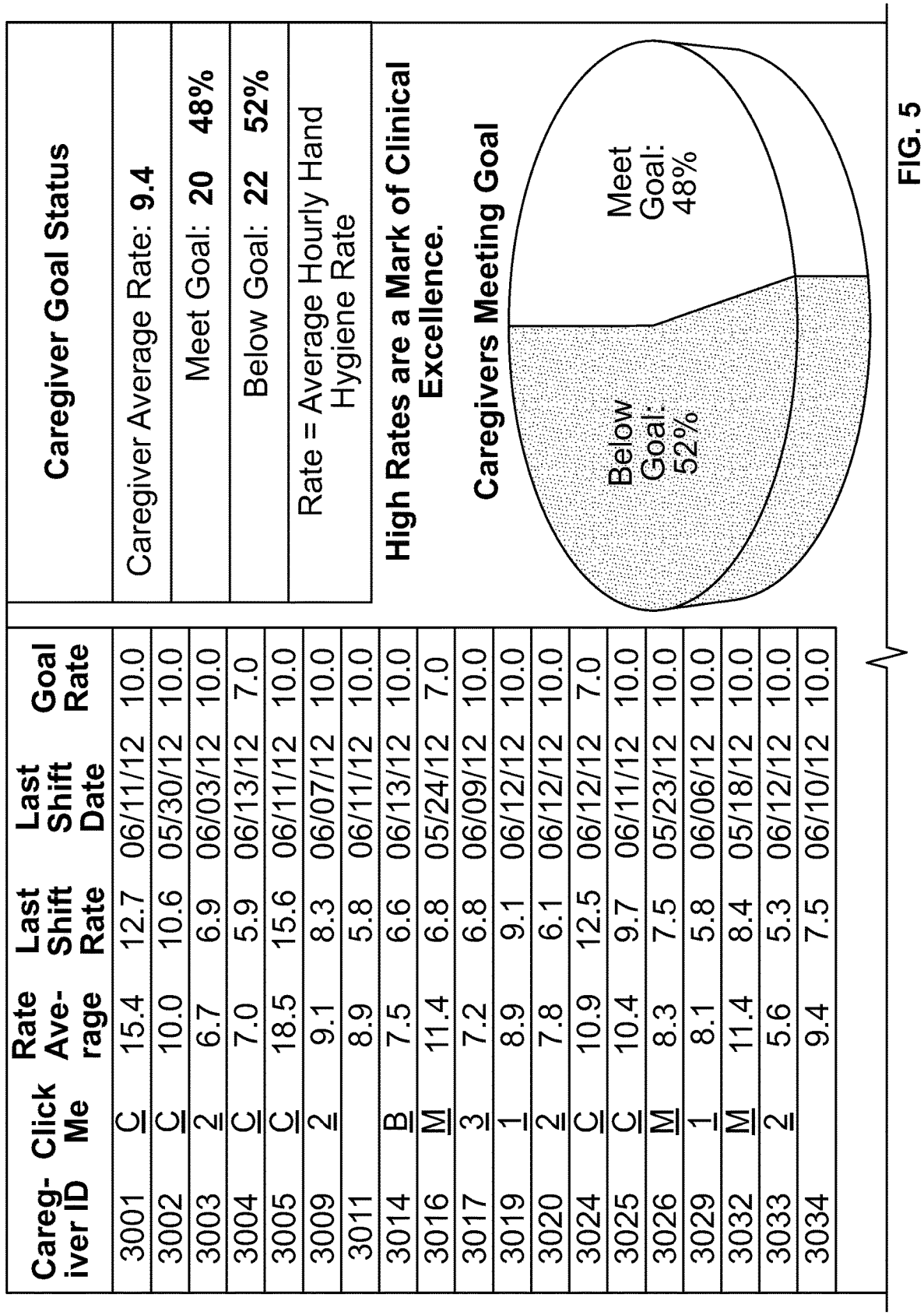
Figure 5:
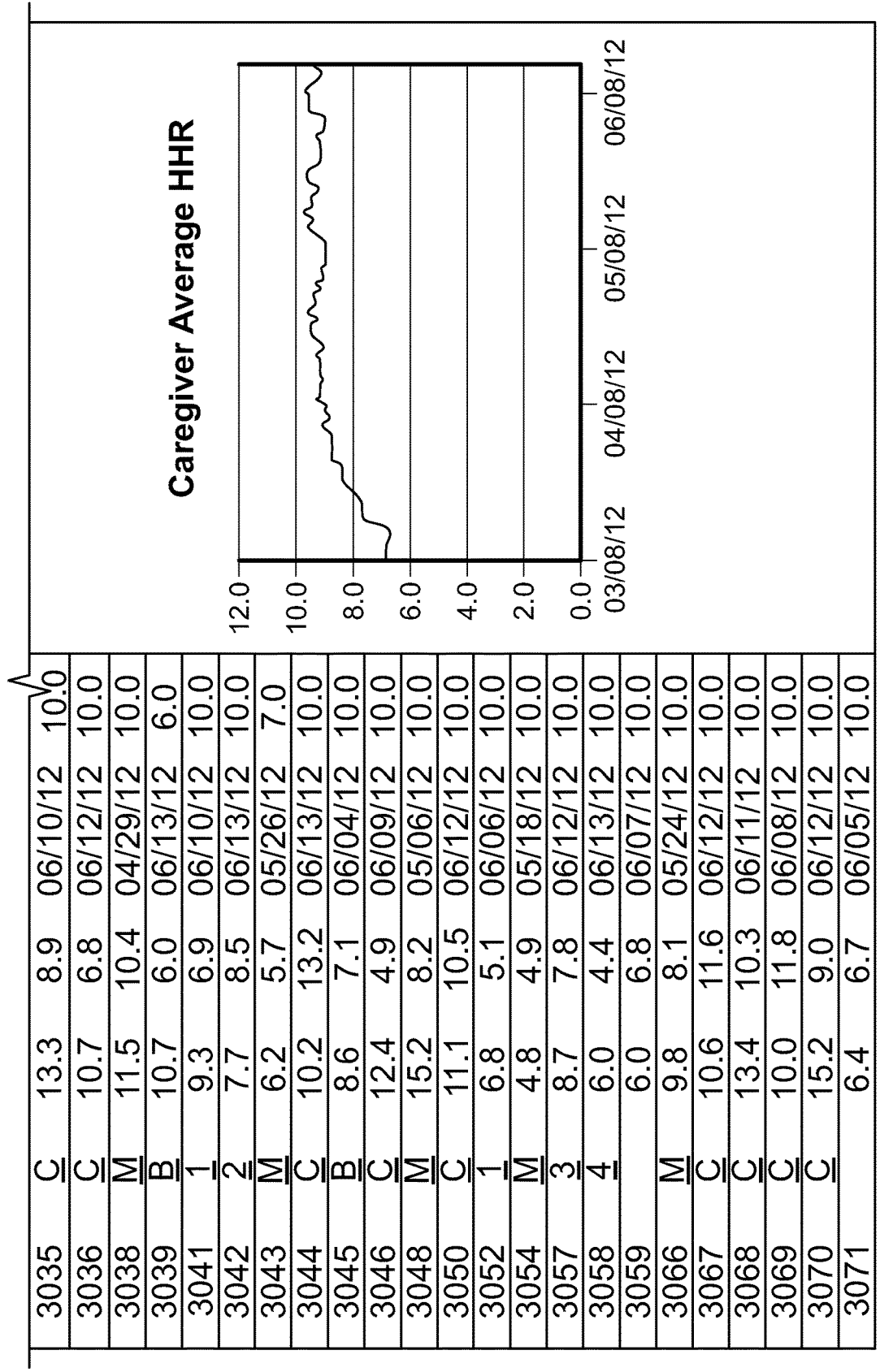

As shown in FIGS. 4 and 5, the system can be configured to display the user or caregiver's average rate, the number of users or caregivers meeting the hand hygiene goal, and the number of users or caregivers below the goal. The display can also be configured to display each individual user rate average, last shift rate, last shift date, time in discrete clinical areas, and goal rate by ID number to maintain confidentiality. The system can also be configured to track certain groups of individuals and to determine average group hand hygiene rates. In the example shown in FIG. 4, the teams are categorized by color, for example, Blue, Pink, Orange, Purple, and Yellow. As shown in the example in FIG. 4, the Blue group has the highest rate of performance. This may help individual users to try to get their rates higher to compete with other groups within a particular facility.

Figure 6:
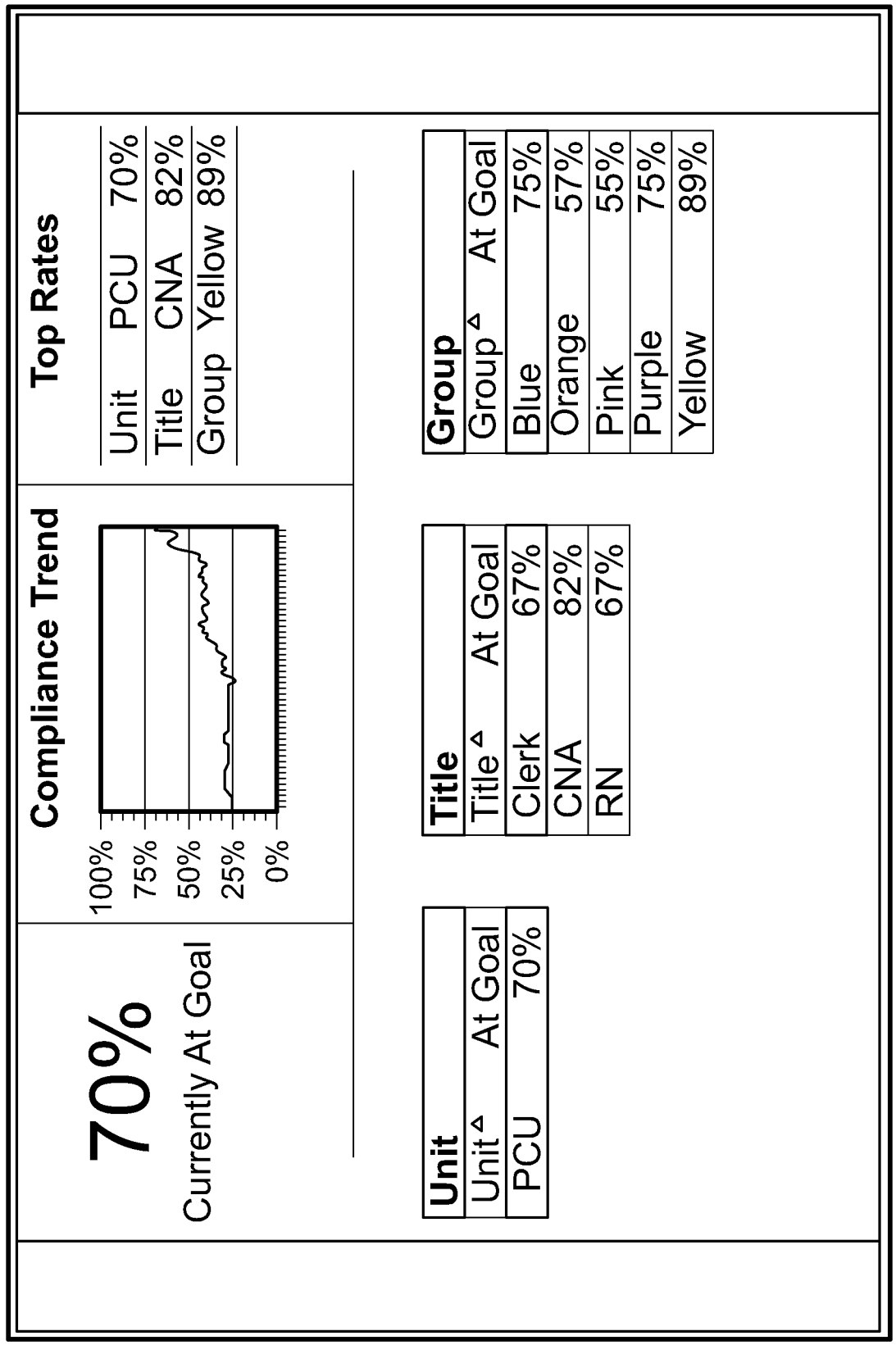
Figure 7:
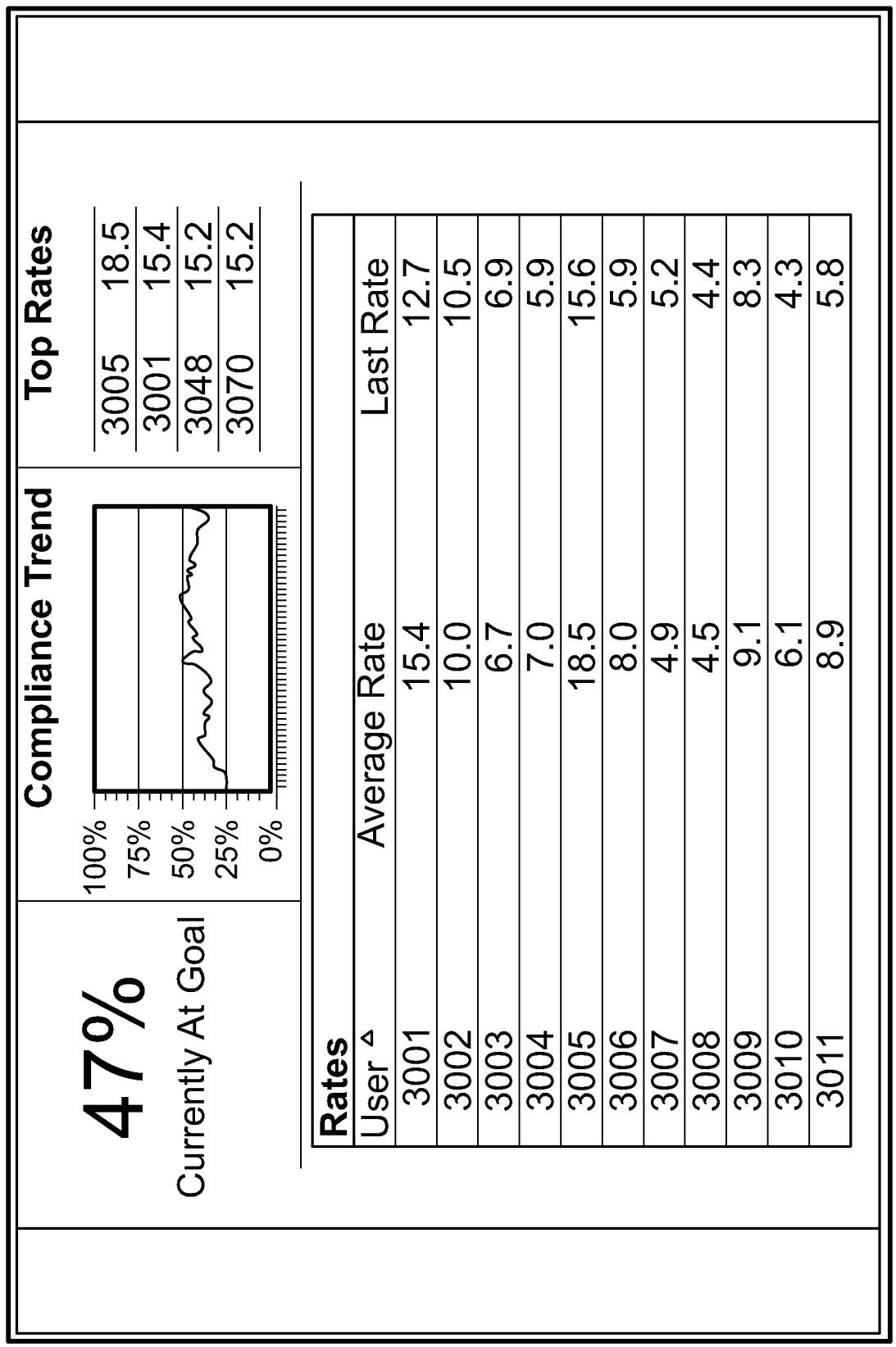

As depicted in FIGS. 6 and 7, the system can be configured to display compliance trends over a predetermined time period and top rates for particular individuals, groups, units and professionals such as nurses or clerks.

Figure 8:
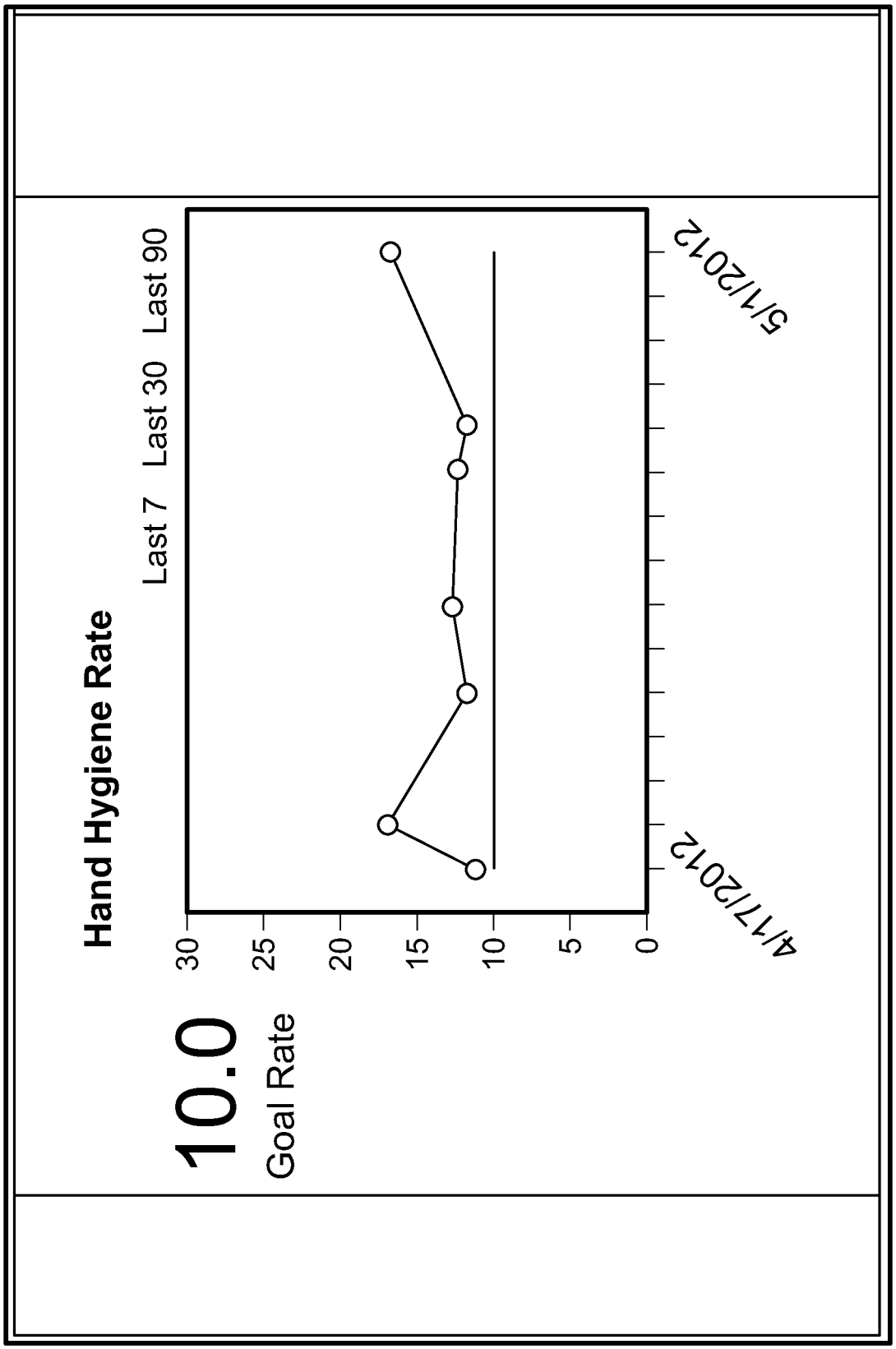

As shown in FIG. 8, the user can get his or her personal hygiene rate over a predetermined or specified time period to view his/her compliance rate over various shifts.

FIGS. 13A-13G show another exemplary personal hand hygiene dispenser 308.

Figure 13A:
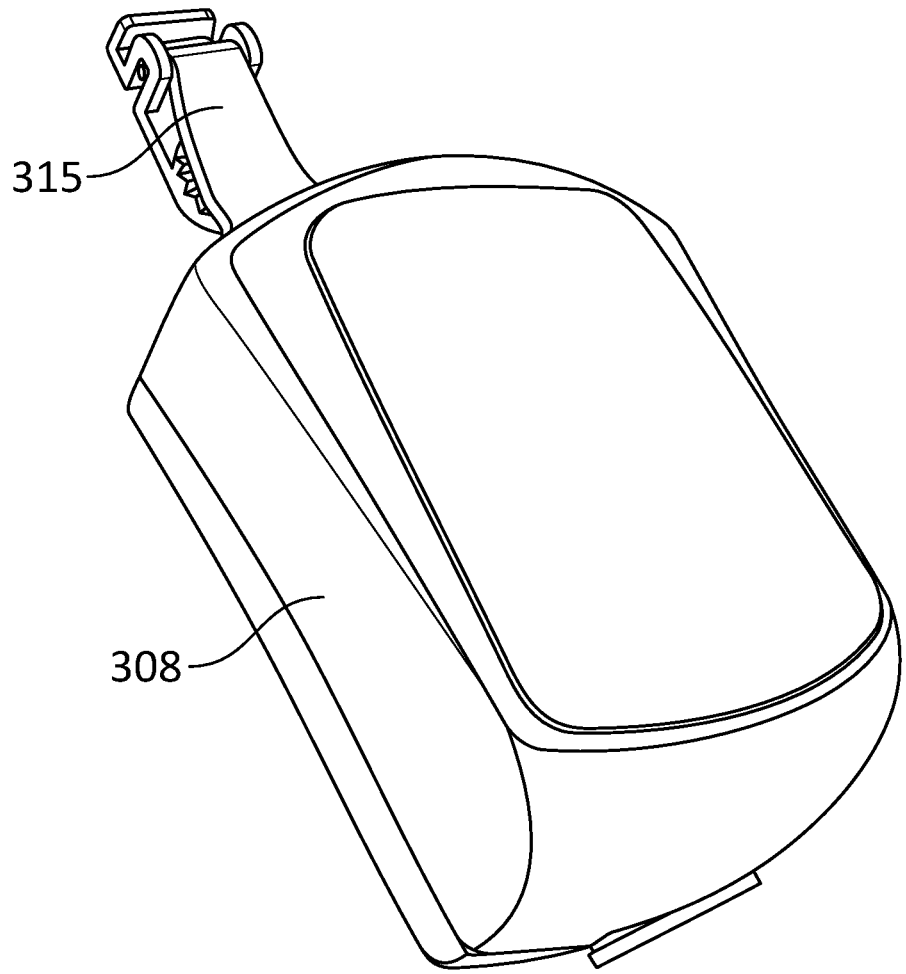
FIG. 13A shows a front perspective view of another example hand hygiene dispenser.
Figure 13B:
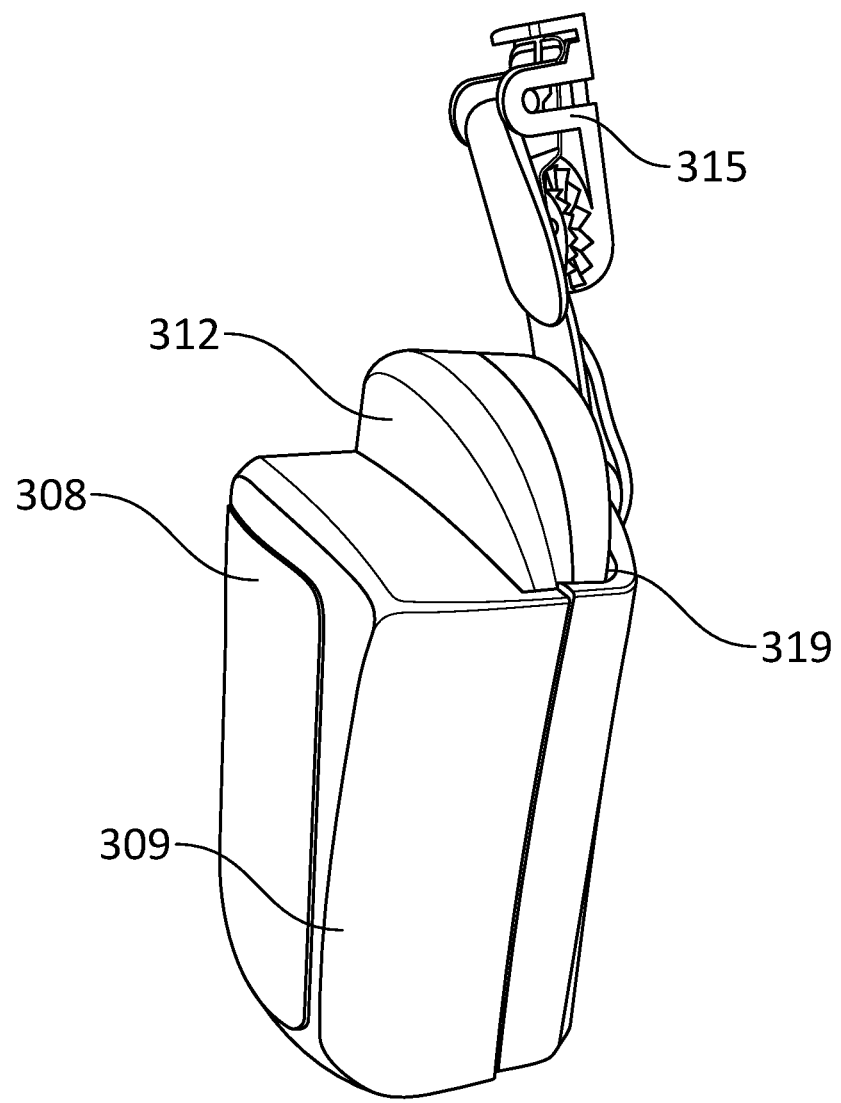
FIG. 13B shows a side perspective view of the example hand hygiene dispenser of FIG. 13A.
Figure 13C:
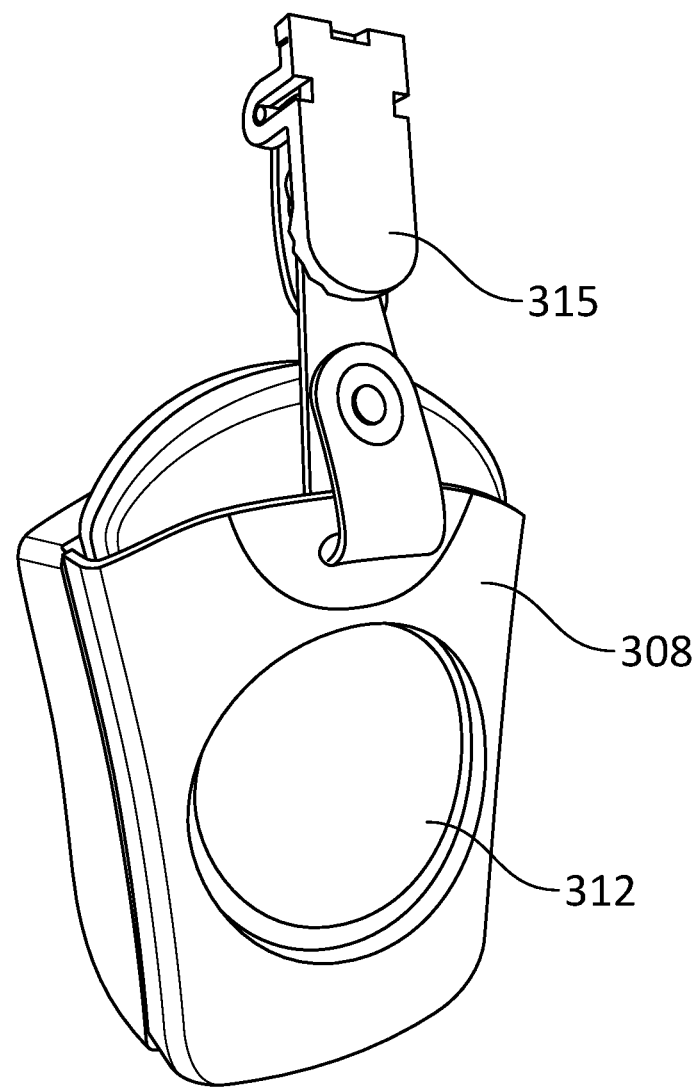
FIG. 13C shows a rear perspective view of the hand hygiene dispenser of FIG. 13A.
Figure 13D:
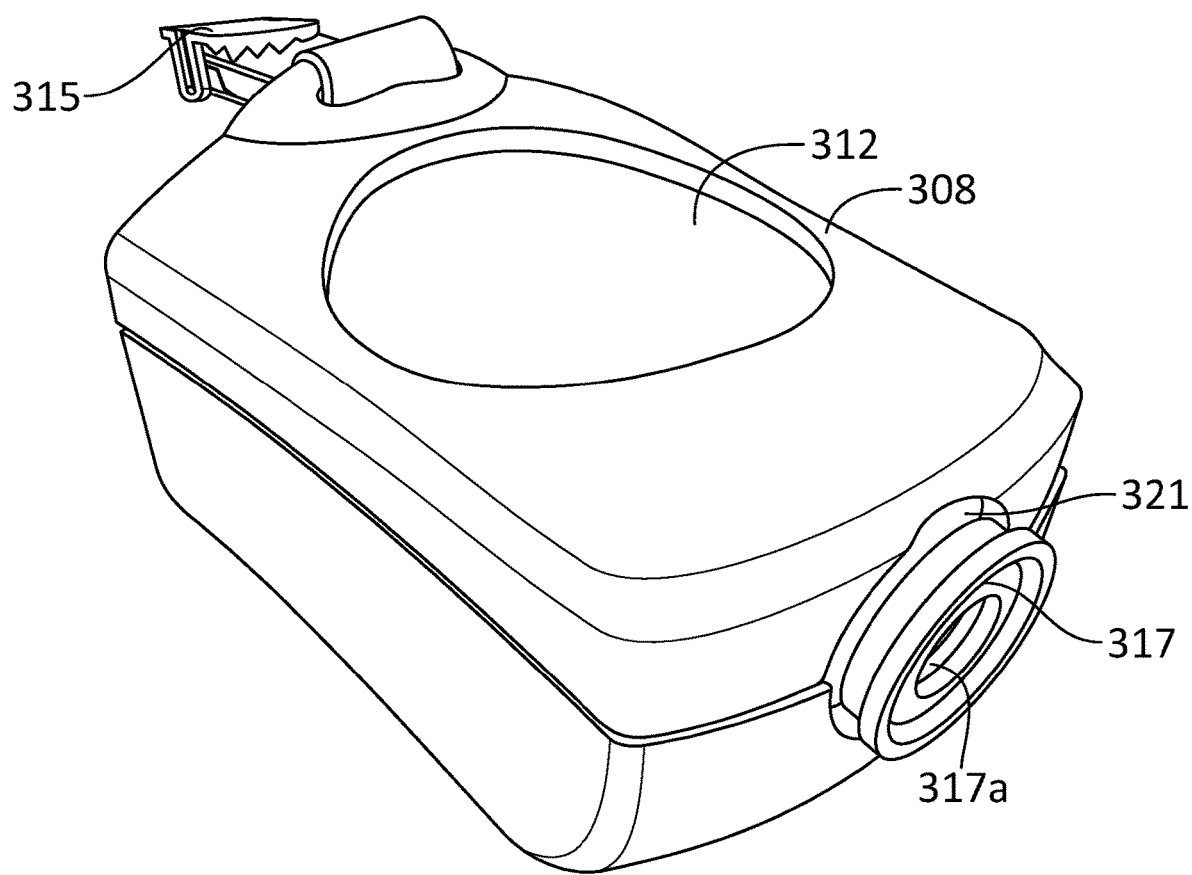
FIG. 13D shows a bottom perspective view of the hand hygiene dispenser FIG. 13A.
Figure 13E:
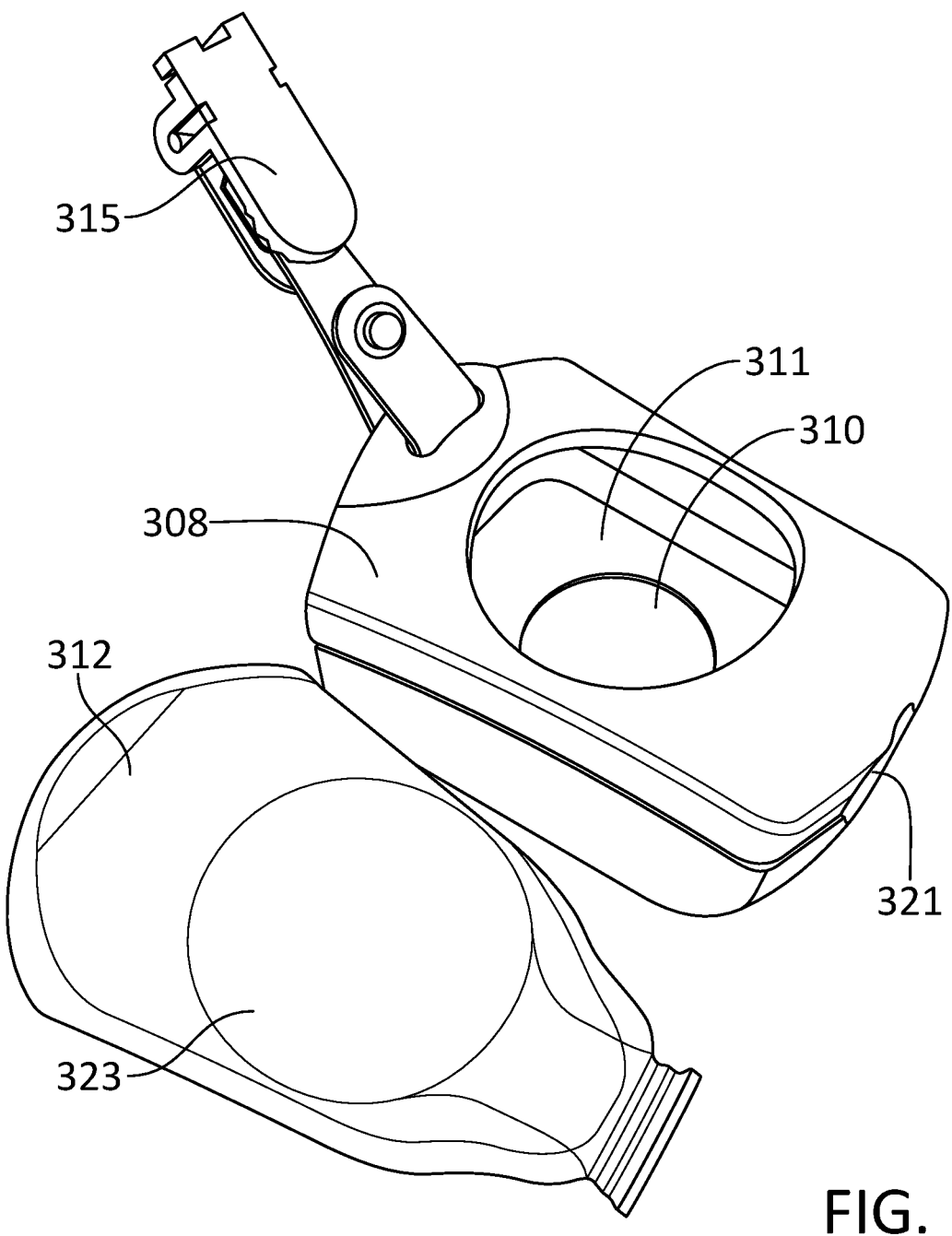
FIG. 13E shows an alternate configuration of the hand hygiene dispenser of FIG. 13A.
Figure 13F:
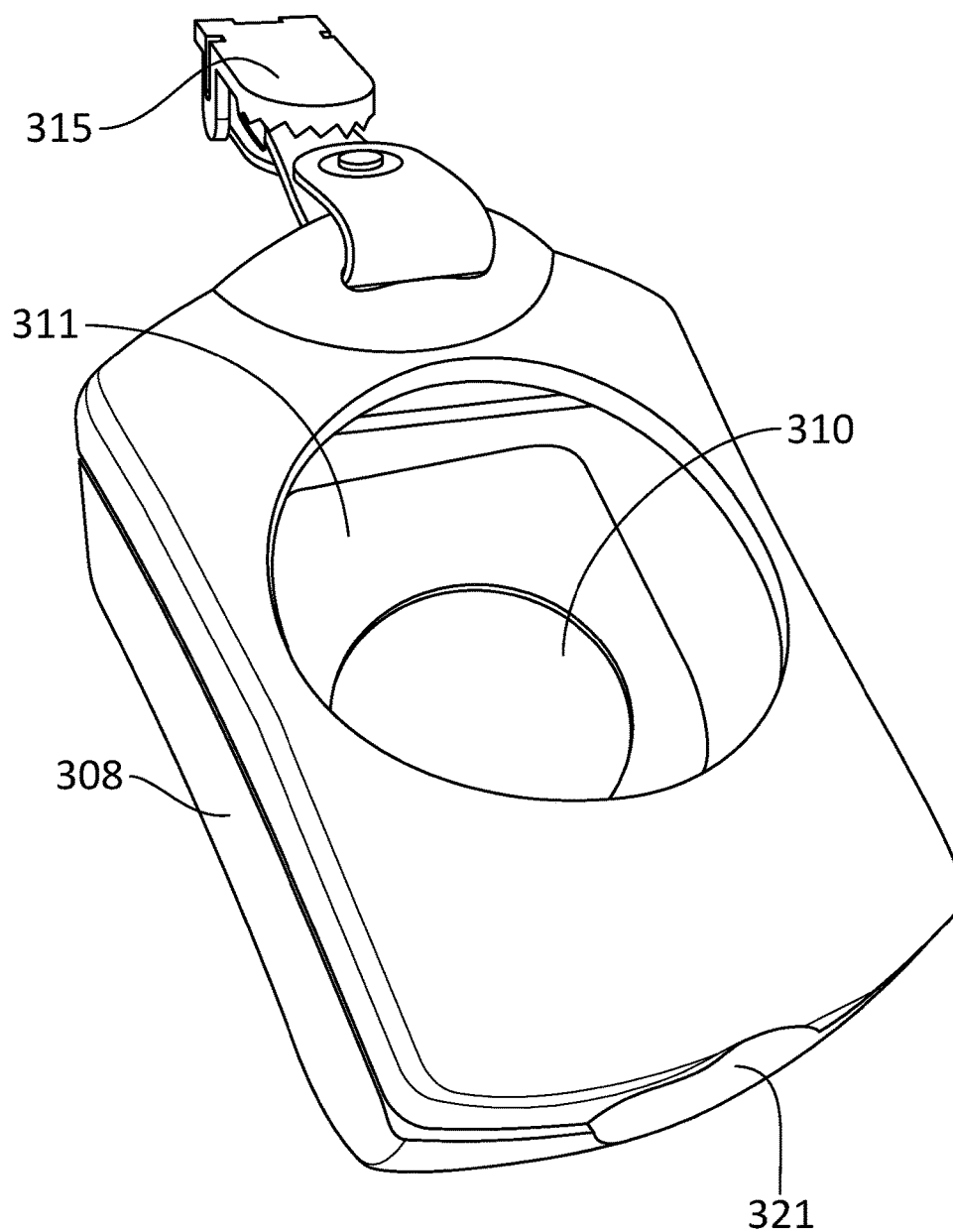
FIG. 13F shows a rear view of an alternate configuration of the hand hygiene dispenser of FIG. 13A.
Figure 13G:
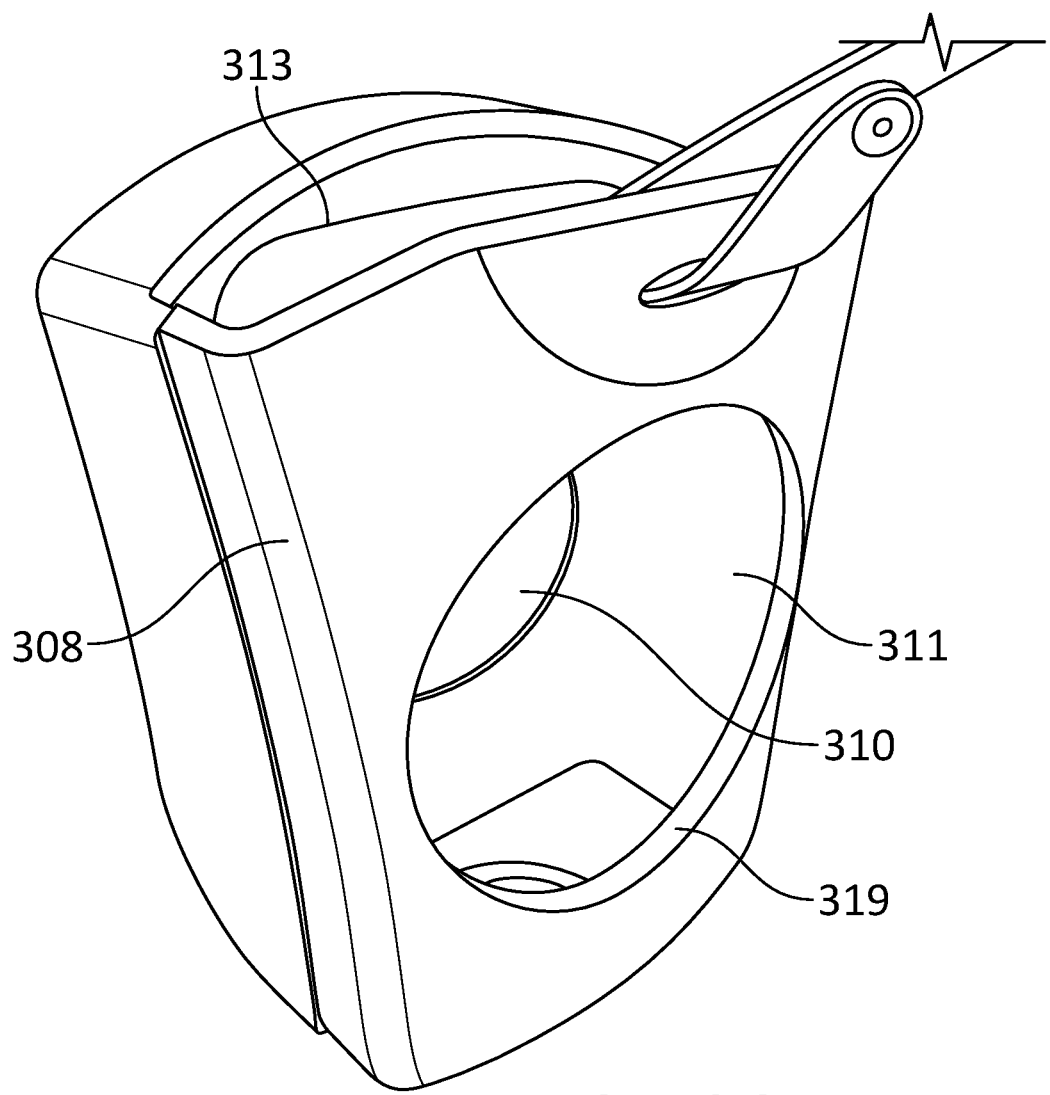
FIG. 13G shows another rear perspective view of an alternate configuration of the hand hygiene dispenser of FIG. 13A.

FIG. 13A generally shows a front perspective view of the example hand hygiene dispenser 308. FIG. 13B shows a side perspective view of the example hand hygiene dispenser 308. FIG. 13C shows a rear perspective view of the hand hygiene dispenser 308. FIG. 13D shows a bottom perspective view of the hand hygiene dispenser 308. FIG. 13E shows the hand hygiene dispenser with the container 312 removed. FIG. 13F shows a rear view of the hand hygiene dispenser 308 with the container 312 removed. FIG. 13G shows another rear perspective view of the hand hygiene dispenser 308 with the container 312 removed.

Figure 3D:
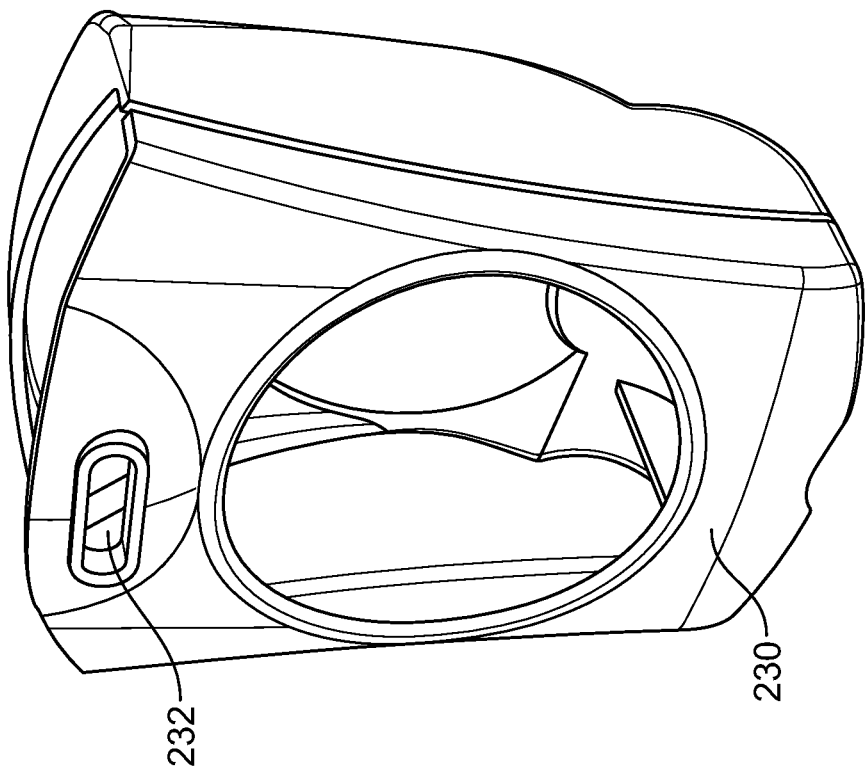
FIG. 3D depicts another perspective view of the exemplary embodiment in accordance with FIG. 3A.
Figure 3C:
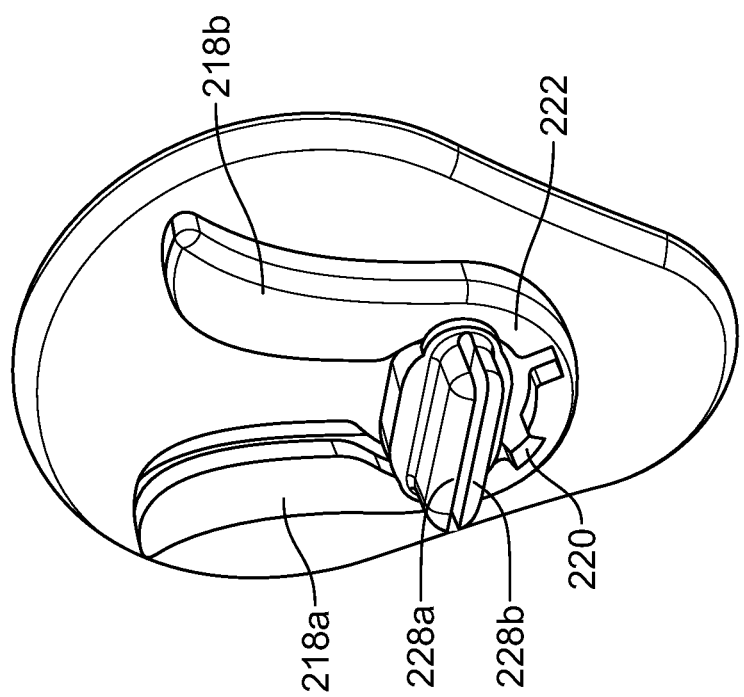
FIG. 3C depicts another perspective view of the exemplary embodiment in accordance with FIG. 3A.

The dispenser 308 can include the same or similar features and can include the same or similar functionality as the hand hygiene dispenser as discussed herein in relation to FIGS. 3-3D in which like reference numerals indicate similar elements.

As shown in FIGS. 13A-13G, the personal hand hygiene dispenser 308 generally includes a housing 309 which includes an internal recess 311 (shown in FIG. 13G) for holding a bottle or container 312 having an internal reservoir for hand sanitizer. The internal recess is connected with a top recess 313 (shown in FIG. 13G) for inserting the container 312 into the housing and a bottom recess 321 (shown in FIGS. 13D and 13F) for receiving a spout 317 which defines an opening 317a of the container 312. Additionally the housing 309 can be provided with a circular opening 319 for viewing the container 312, which provides the user with a visual indication of how much hand sanitizer is left in the container 312. The opening 319 can also provide direct contact with the container 312 and the user's hand such that the hand sanitizer will easily dispense from the container 312.

Within the recess 311 of the housing 309, an input or sensor 310 is included for sensing when a hand hygiene event occurs. As shown in FIG. 13E-13G, the input 310 can be located within the housing 309. An attachment mechanism 315 can also be included for attaching the dispenser 308 to a health care worker's clothing or lanyard.

Additionally, like in the above example, the dispenser 308 may also include an RF, IR, or other known type of wireless transmitter, memory circuit, and a light indicator for indicating a hand hygiene event once the input 310 is depressed. Additionally, the hand hygiene dispenser 308 can include a processor, RAM, ROM, and a memory for storage to provide instructions to the processor for enabling the hand hygiene dispenser 308 to perform various functions or for storing the dispensing actions, which can be downloaded at a later time. This minimizes the use of power by the hand hygiene dispenser 308.

Alternatively or in addition, the hand hygiene dispenser 308 can be configured to communicate with various connection points throughout a facility. For example, the above connections can be made via the internet, Ethernet, Bluetooth, Wi-Fi, cell modems, or infrared. In one specific example, the above connections can be made using a reduced power consumption type of communication or low-power radio signals, e.g., Bluetooth Low Energy (also referred to as "Bluetooth LE," "Bluetooth Smart," or "BLE"), Zigbee, and ISM. In one example, the ISM can be an NFC connection. For example, the dispenser computer can store a number of previous hand hygiene events and then transmit the hand hygiene events to the various connection points throughout the facility when the dispenser is within a certain range, e.g., 5-100 meters. Other known techniques for transferring the data from the dispensers 308 to the server are also contemplated.

As shown in FIG. 13D, the contents of the container 312 are squeezed through an opening 317a in the bottom of the dispenser 308 to dispense the hand sanitizer located in the container 312. In addition to dispensing hand sanitizer from the dispenser 308, squeezing the container 312 also activates the input 310. As shown in FIGS. 13E-13G, the input 310 is located within the housing 309 so that the container 312 abuts the input 310. As shown in FIG. 13E, the container 312 can be included with opposing walls 323. When the container 312 is placed in the hand hygiene dispenser housing 309, one of the walls 323 will be placed into contact with the input 310 and the other wall will be partially viewable through the opening 319.

In this way, when the user squeezes the housing 309 and the container 312 to dispense hand sanitizer, the wall 323 of the container 312 in contact with the input 310 will displace the input 310, which signals that a hand hygiene event has occurred. Moreover, when the input 310 is displaced or actuated, a hand hygiene event will be stored in the memory of the hand hygiene dispenser 308. The hand hygiene event can be later downloaded or transmitted from the hand hygiene dispenser 308 as discussed herein. In one specific example, the input 310 sends a signal to the processor, which stores the hand hygiene event in the memory of the dispenser 308 to record the event for later downloading to a computer (e.g., receiving and transmitting station as discussed below) or when the hand hygiene dispenser 308 is synced during a shift or at the end of the workday.

In alternative examples, it is contemplated that when the container 312 is squeezed, the input 310 is pressed simultaneously to send a signal via a transmitter and antenna to indicate to the server that a hand hygiene event has occurred. The transmitter can be connected to the input 310, which sends a signal to the network indicating that a hand hygiene event has occurred. Additionally, the actuation of the input 310 may be associated with a time interval that is stored in the memory circuit and represents the time and date of each activation.

Locating the input 310 within the housing 309 provides a more accurate reading of when a hand hygiene event occurs. For example, it prevents accidental actuation of the input 310 and prevents users from cheating by preventing the detection of a hand hygiene event, unless the container is also fully squeezed within the housing 318. It also provides a more robust design of the dispenser 308 since the input 310 is not externally exposed in anyway. As discussed below in relation to FIGS. 14A and 14B, in one example, the input 310 can be configured as a push button switch, which can be an analogue or electrical switch and may include one or more relays or transistors. However, other known switch types and sensor types are contemplated.

Like in the above example, the container 312 can be a refillable reservoir or can be implemented as a replaceable cartridge. As shown in FIGS. 13E-13G, the container 312 can be removed from the housing 318 and replaced with a full container 312 or the container 312 can be refilled with hand sanitizer and placed back in the housing 308. In particular, similar to the example discussed above, as shown in FIGS. 13F and 13G, the container 312 can be inserted and removed through the top recess 313 and is held into place in the housing 318 by an interference or friction fit.

Additionally, the dispenser 308 may include an accelerometer for detecting user motion as discussed in further detail below. This allows the system to determine whether the dispenser 308 is in use to assist with proper calculation of a hand hygiene rate. For example, if the accelerometer detects motion of the dispenser, the system 308 can detect that a user is wearing and using the device. However, if the accelerometer is not detecting any motion, then it can be determined that the user has removed the dispenser from his/her clothing and the dispenser is not in use.

In yet another example, as in the examples discussed above, the dispenser 308 may also include a display screen (not shown) for displaying performance data, such as the user's average dispensing rate, to the user. The display can also display data from a group, such as a unit or facility hand hygiene rate, and other current and historical data. The hand hygiene dispenser 308 can include various input devices such as buttons, keys, or a touchscreen. In one example, an input device can provide the user with the ability to scroll through current and historical hand hygiene data and may also have an input for turning the display on and off to maintain privacy. In one particular example, the display screen can be configured as a touch screen providing an interface for viewing the desired content.

Figure 14B:
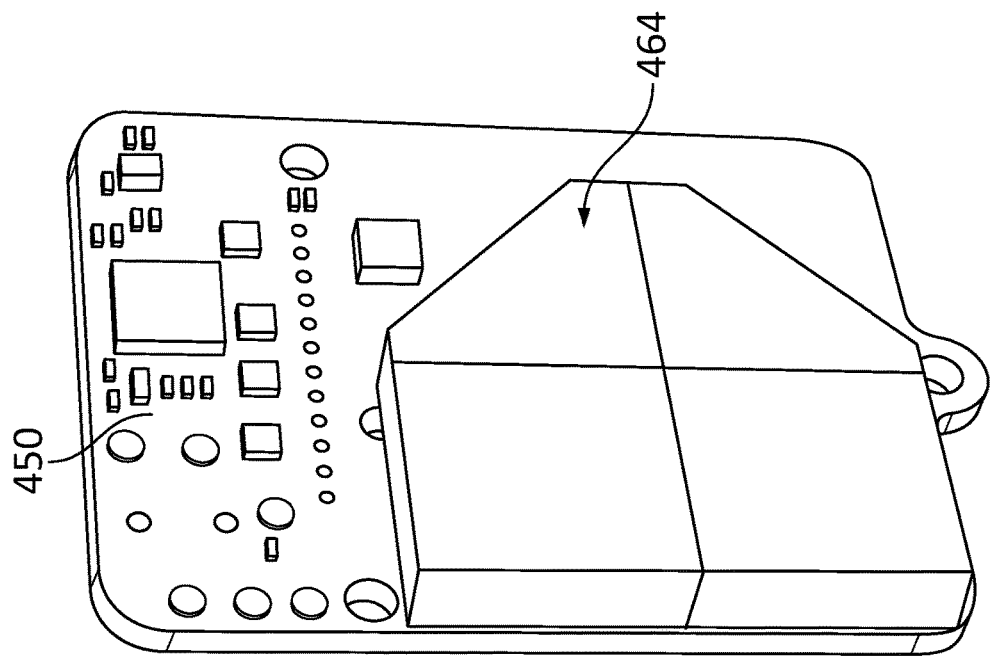
FIGS. 14A and 14B depict an example printed circuit board for a hand hygiene dispenser.
Figure 14A:
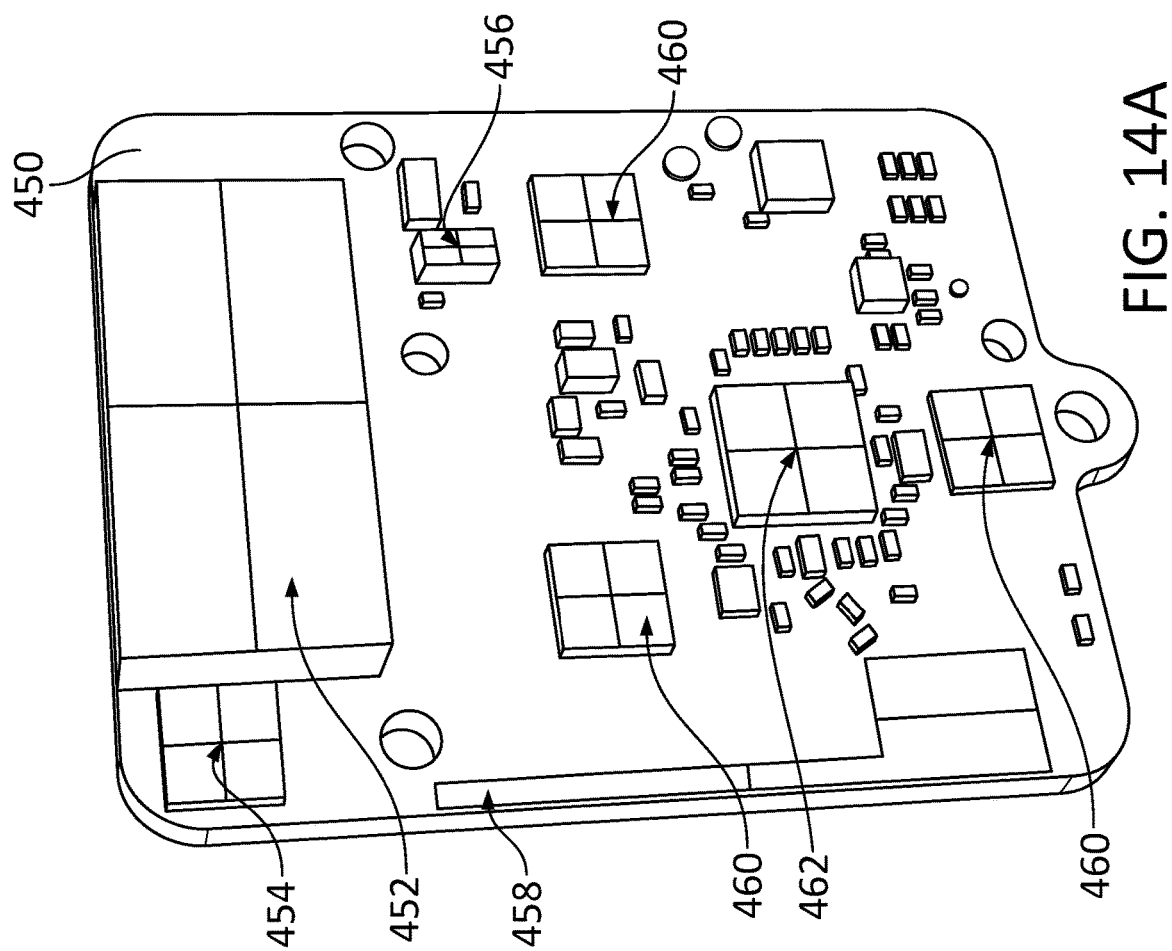

FIGS. 14A and 14B depict an exemplary printed circuit board (PCB) 450 for a hand hygiene dispenser, where FIG. 14A shows a front perspective view and FIG. 14B shows a rear perspective view of the PCB. As shown in FIGS. 14A and 14B, the PCB 450 can include an LCD screen 452, an LCD control button 454, an accelerometer 456, an antenna 458, inputs 460, a microprocessor 462, and a battery 464. Each of the LCD screen 452, the LCD control button 454, the accelerometer 456, the antenna 458, the inputs 460, and the battery 464 can be connected to the microprocessor 462, which can be configured to receive and send inputs to each of the PCB components.

In accordance with the examples above, the LCD control button 454 can be configured to turn the LCD screen on for viewing the various hand hygiene data discussed herein, and the LCD control button can be configured to turn the LCD screen off for privacy purposes. The LCD control button 454 can also be configured with scrolling and toggling capabilities to view various portions of hand hygiene data such as personal hand hygiene rates, group hygiene rates, or facility hygiene rates.

Also the PCB 450 can include an antenna 458, which can be configured to wirelessly transmit or receive hand hygiene information via any wireless transmission protocol. In one example, as discussed herein the transmission protocol can be a form of low energy transmission, such as Bluetooth Low Energy (also referred to as "Bluetooth LE," "Bluetooth Smart," or "BLE"), Zigbee, or ISM. The PCB 450 may also include the accelerometer 456 for detecting motion of the hand hygiene dispenser 308.

The accelerometer 456 can include various components for converting mechanical motion to electrical signals, such as piezoelectric, piezoresistive, and capacitive components.

The microprocessor 462 can receive signals from the accelerometer 456 indicating when the hand hygiene dispenser 308 is undergoing movement. Further, the microprocessor 462 can include instructions that determine the length of an evaluation period based on the amount of time that the accelerometer is undergoing movement, and after a predetermined amount of time or time interval, the microprocessor 462 can determine that the hand hygiene dispenser 308 is no longer in use. In this way, the hand hygiene dispenser 308 can be configured to more accurately determine the hand hygiene rate.

In another example, the accelerometer data can also be used to determine how many steps are taken in a day by the health care worker. This data can be utilized to determine whether a user is applying an appropriate amount of hand sanitizer during a shift. Additionally the accelerometer data can be used to trigger a signal that can be sent to the user through the user's hand hygiene device. For example, if a user is stops to see a patient and is stationary for a predetermined amount of time, the accelerometer can detect the user has stopped and send a reminder signal to the user to dispense hand sanitizer from the hand hygiene dispenser.

In another example, the accelerometer data can be stored in a database and can be used to identify work and motion patterns for varied clinical roles. For example, a health care worker in an ER will have different activity level than a health care worker in a doctor's office or intensive care unit. The work and motion patterns can be analyzed with predetermined templates for each health care worker type e.g., the appropriate level of hand hygiene events for the particular health care worker type. For example, the health care worker's motion and hand hygiene event data can be compared to the templates for the appropriate clinicians to automatically make suggestions on how to improve appropriate clinical hand hygiene performance. As discussed herein, these suggestions can be made in the form of text, icons, or audible reminders on the personal hygiene dispensers, in emails or texts to the users or other electronic methods.

The templates can be created by calculating ideal hand hygiene rates and activity level for each worker type or from historical data from the particular worker type. For example, the motion information and hand hygiene information can be collected and used to identify motion and hand hygiene patterns. The motion and hand hygiene patterns are then used to create templates for evaluating hand hygiene data.

The PCB 450 can also be provided with various inputs 460 that can be configured to detect hand hygiene events. In one example, the inputs 460 can be configured as event buttons. The inputs 460 detect when the user dispenses hand sanitizer from the hand hygiene dispenser. In this example three inputs 460 can be provided for redundancy purposes to ensure that a hand hygiene event is detected. However, it is also contemplated that one or two inputs could be included on the PCB 450. In multiple input examples, it is contemplated that a control circuit can be included to ensure that the pressing of multiple inputs simultaneously does not count for more than one hand hygiene event. For example, instructions can be stored in the memory and provided to the processor to count only one hand hygiene event when the inputs are triggered with control logic. Additionally, the control circuit may only count one hand hygiene event when the inputs 460 are triggered at close intervals. In other examples, the switches can be wired in parallel such that only one event is detected. The circuit could also be provided with one or more relays to ensure that the multiple switches do not detect more than one hand hygiene event. In one example, the inputs 460 can be configured as push button switches and can be analogue or electrical switches and may include one or more relays or transistors. However, other known switch types are contemplated.

As shown in FIG. 14B, the PCB can also be included with a rechargeable battery 464, such as a lead-acid, nickel cadmium (NiCd), nickel metal hydride (NiMH), lithium ion (Li-ion), and lithium ion polymer (Li-ion polymer) type batteries or any other batteries suitable for consumer electronic devices. The battery 464 can be recharged at the end of a shift or day by plugging the hand hygiene dispenser into an outlet or computing device (e.g. USB). For example, the hand hygiene dispenser can be provided with a power adapter for supplying power to internal charging circuitry within the hand hygiene dispenser for the battery 464. Additionally, it is also contemplated that facilities can be outfitted with charging kiosks that can be configured to charge the hand hygiene dispensers throughout the workday, such as during breaks of the healthcare workers.

Figure 15A:
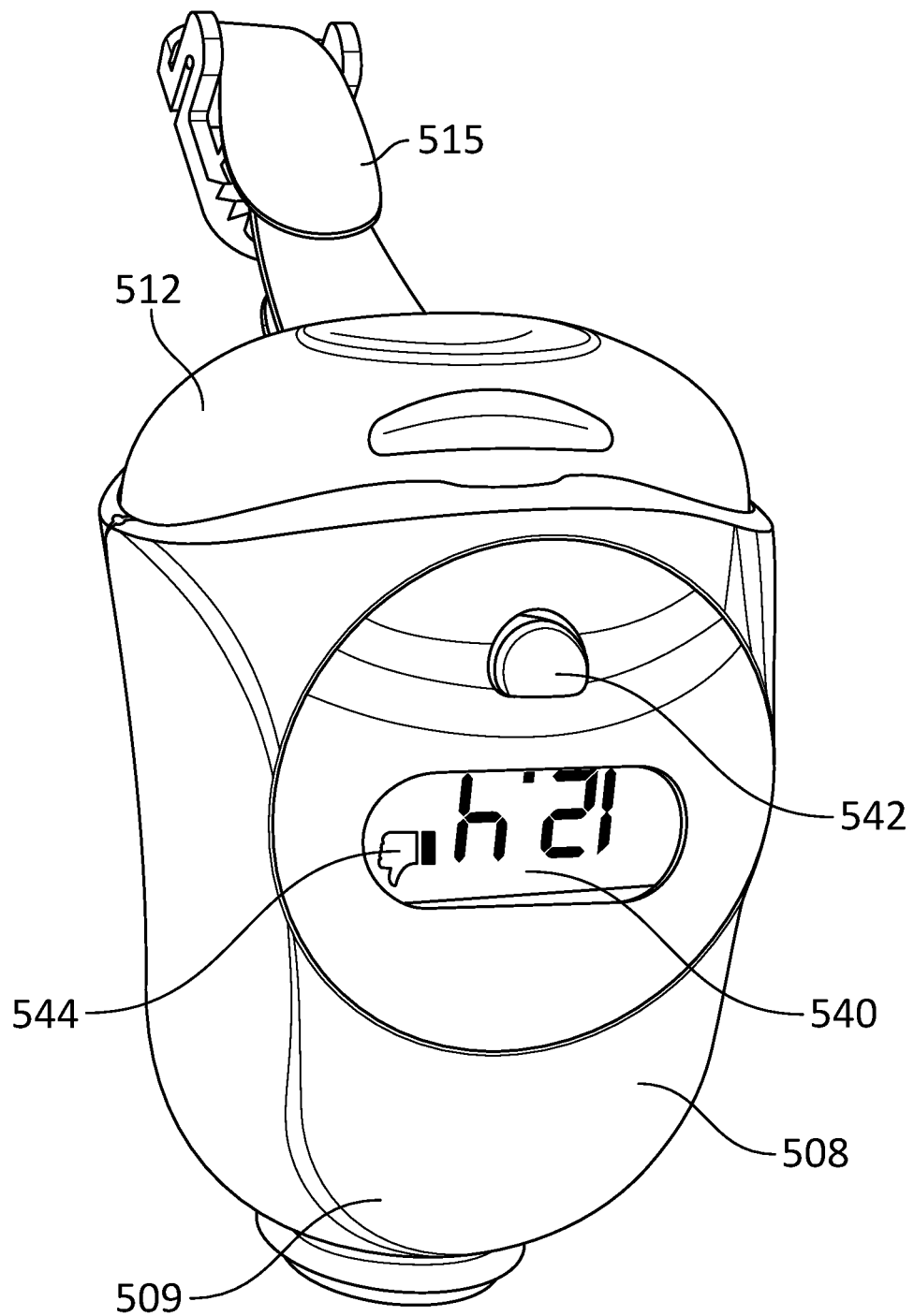
FIG. 15A shows a front perspective view of another example hand hygiene dispenser.
Figure 15B:
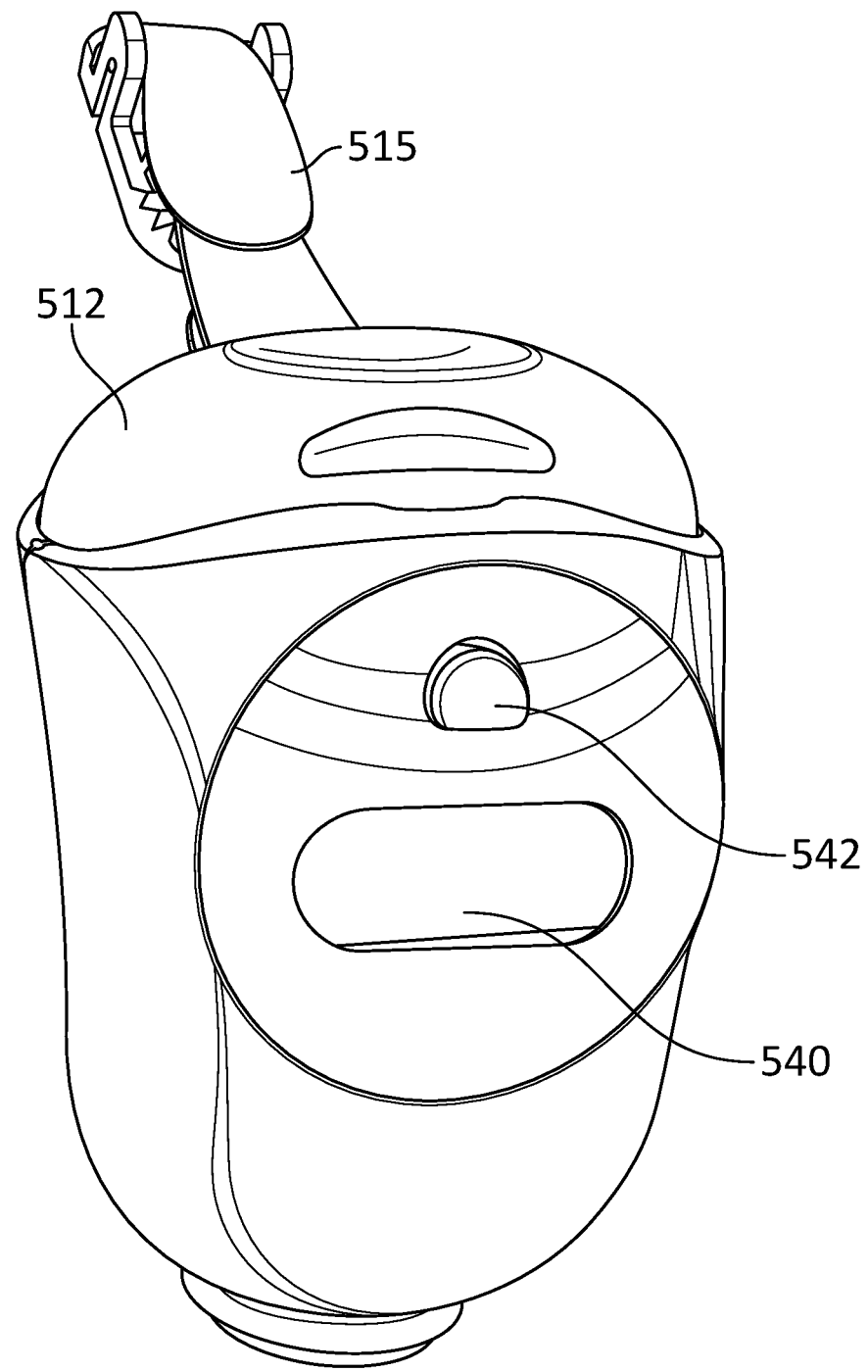
FIG. 15B shows another front perspective view of the example hand hygiene of FIG. 15A in another configuration.
Figure 15C:
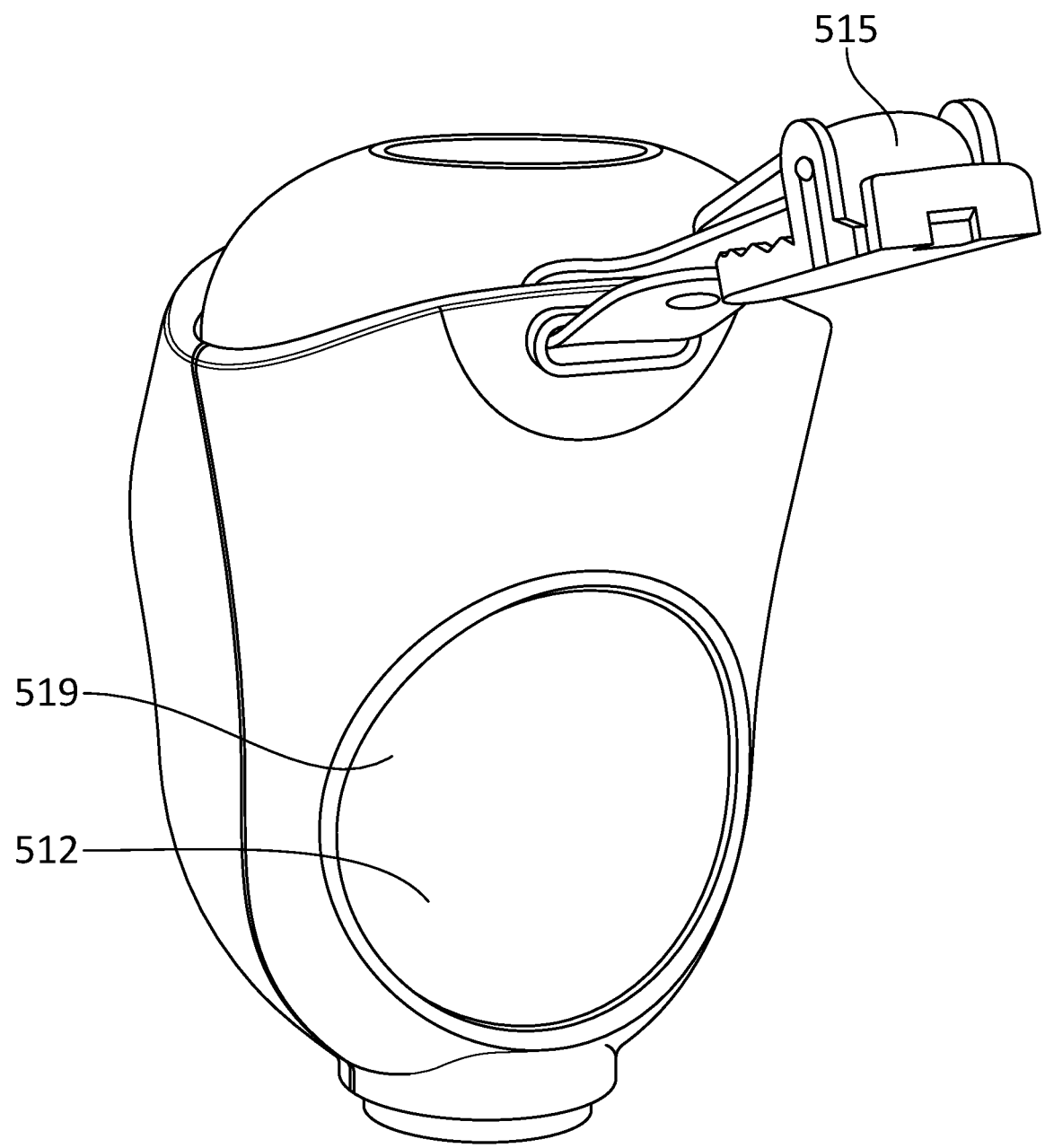
FIG. 15C shows a rear perspective view of the example hand hygiene dispenser of FIG. 15A.
Figure 15D:
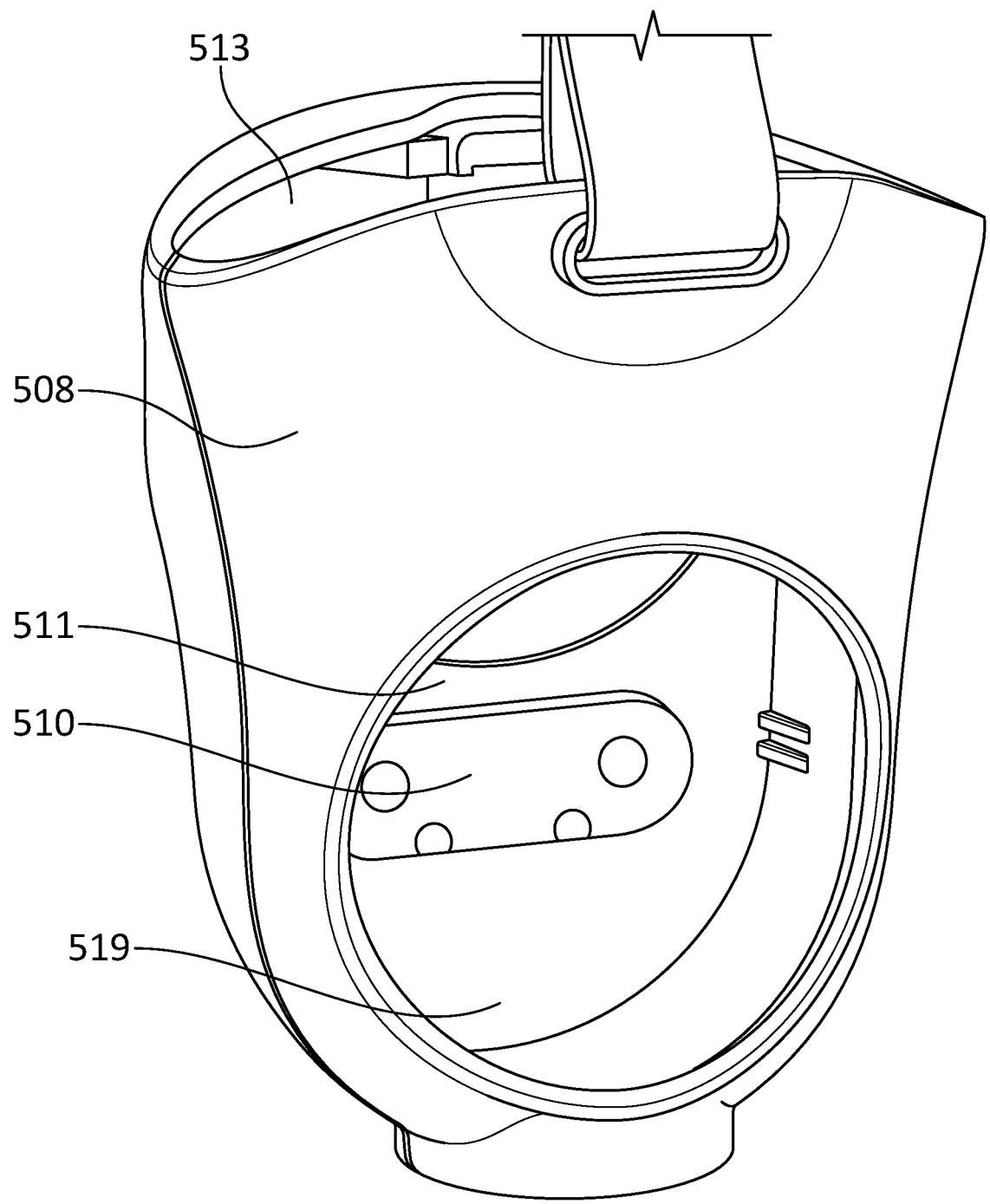
FIG. 15D shows a rear perspective view of the hand hygiene dispenser of FIG. 15A in another configuration.

FIGS. 15A-15D show another exemplary personal hand hygiene dispenser 508. FIG. 15A generally shows a front perspective view of the example hand hygiene dispenser 508. FIG. 15B shows another front perspective view of the example hand hygiene dispenser 508 in another configuration. FIG. 15C shows a rear perspective view of the hand hygiene dispenser 508. FIG. 15D shows a rear perspective view of the hand hygiene dispenser 508 with the container 512 removed.

The dispenser 508 can include the same or similar features and can include the same or similar functionality as the hand hygiene dispenser as discussed herein in relation to FIGS. 3-3D and 13A-13G in which like reference numerals indicate similar elements. In this example, the hand hygiene dispenser 508 can include a display screen 540.

The display screen 540 can be configured to display screen performance data, such as the user's average dispensing rate, to the user. The display screen 540 can also display data from a group, such as a unit or facility hand hygiene rate, and other current and historical data. The display screen 540 can also be configured to indicate whether the user is meeting their hand hygiene goals with various symbols or icons 544. In one example, the icon 544 can be a "thumbs up" to indicate that the user is in compliance, or a "thumbs down" to indicate that the user needs to clean his/her hands more. The display screen 540 can also provide certain other alerts to the user such as low battery, low hand sanitizer amount, etc. It is also contemplated that the display screen 540 can be configured to provide various different views of data and alerts for the user.

Additionally, the display screen 540 can be provided with an input device 542, which can provide the user with the ability to scroll through current and historical hand hygiene data and may also be configured to turn the display on or off to maintain privacy. It is contemplated, however, that the hand hygiene dispenser 508 can include various other input devices such as buttons, keys, or a touchscreen. For example, the display screen 540 can be configured as a touch screen providing an interface for viewing the desired content.

Similar to the example shown in FIGS. 13A-13G, the personal hand hygiene dispenser 508 generally includes a housing 509 which includes an internal recess 511 (shown in FIG. 15D) for holding a bottle or container 512 having an internal reservoir for hand sanitizer. The internal recess is connected with a top recess 513 (shown in FIG. 15D) for inserting the container 512 into the housing 509 and a bottom recess for receiving a spout, which defines an opening of the container 512. Additionally the housing 509 can be provided with a circular opening 519 for viewing the container 512, which provides the user with a visual indication of how much hand sanitizer is left in the container 512.

Again similar to the above example, within the recess 511 of the housing 509 an input or sensor 510 is included for sensing when a hand hygiene event occurs. As shown in FIG. 15D, the input 510 can be located within the housing 509. An attachment mechanism 515 can also be included for attaching the dispenser 508 to a health care worker's clothing or lanyard.

The example hand hygiene dispensers can be configured to communicate with any of the devices discussed herein. In one particular example, several computing devices, which can include the same or similar features and functionality as discussed herein in relation to FIGS. 1 and 2, may be provided in the network and set up as receiving and transmitting stations. The receiving and transmitting stations can be dispersed throughout a facility and can form part of a hand hygiene monitoring system. It is contemplated that any computing device could be configured as a receiving and transmitting station, including any computing device within the facility network, and the receiving and transmitting stations may also include an optional display such as an LCD screen. Each of the receiving and transmitting stations can be configured to receive and transmit hygiene data to and from the plurality of hand hygiene dispensers and can display certain data. For example, the hand hygiene dispensers can be configured to send hand hygiene event data to the receiving and transmitting stations. In another example, the receiving and transmitting stations can be configured to transmit various information to the hand hygiene dispensers, such as personal hand hygiene rates, group hand hygiene rates, messages regarding hand hygiene compliance and goals, etc.

In one particular example, one or more computing devices can be configured as receiving and transmitting stations by outfitting one or more computing devices with antennas. The antennas can be configured to receive and transmit hand hygiene data to and from the hand hygiene dispensers via any wireless transmission protocol, including the wireless transmission protocols discussed herein. In one example, as discussed herein, the transmission protocol can be a low energy transmission protocol, such as Bluetooth Low Energy (also referred to as "Bluetooth LE," "Bluetooth Smart," or "BLE"), Zigbee, or ISM. In one example, the antenna can be connected to the computing device via a USB type connection. Additionally, the hand hygiene dispensers and/or the receiving and transmitting stations can be configured to automatically download hand hygiene data from the hand hygiene dispensers or transmit hand hygiene information when the hand hygiene dispenser is within a certain range of a particular receiving station. For example, if a user is out of range from a receiving station, event and motion data can be retained in the user's hand hygiene dispenser until the user is within a predetermined range of the receiving and transmitting station, e.g., 5-100 meters. When the user is within the predetermined range, the data will be automatically downloaded from or transmitted to the hand hygiene dispenser.

The receiving and transmitting stations can also be configured to relay the hand hygiene information from the dispensers to a network or internet for viewing by the facility management and others to determine hand hygiene performance, compliance and areas of improvement. Additionally, the receiving and transmitting stations or the network can be include a data collection module, which can be configured to collect data from each of the hand hygiene dispensers and to store this data into a database, such as an open source database, e.g., MySQL. The receiving stations can also be configured to collect all of the hand hygiene data from all of the hand hygiene dispensers and to transmit this data to a database, which can reside anywhere on the network.

In one exemplary embodiment, an internet-based (online) training system is integrated with the system to help users learn how to best use the personal dispenser and measurement system. The online training program can include text instruction as well as audio and video instruction and commentary. Questions can be posed to the users and their responses can be recorded in an associated database that corresponds with their personal dispenser performance records. The responses can be used to tailor additional online instruction. Users can awarded pass or fail status of the training material based on their correct response rate against an established acceptable percentage of correct answers.

In one exemplary embodiment, a certification component can use performance and/or online training status criteria to achieve and maintain a certification status. Ongoing certification status can be based on established acceptable performance criteria. Also there can be multiple levels of performance certification.

Figure 16:
FIG. 16 depicts an example certificate of clinical excellence.

In one example, the certification component can be based on users' personal dispenser performance data minimum use rate criteria. In particular, certification status can be based on a minimum number of shifts logged by a user's personal dispenser and a given ratio of shift use rates at or above a given goal rate. The primary performance criteria can be 1) a minimum number of shifts recorded by the user's personal dispenser during a given time interval, e.g., six shifts a month, 2) a minimum percentage of shifts at or above the user's goal rate during a given time interval i.e. one third of the shifts during a month are at or above the goal rate of 6.0. Rating levels can be based on the percentage of shifts at or above goal, e.g., "Proficiency" rating is for one-third to two-thirds of shifts at or above goal and "Excellence" rating is for more than two-thirds of shifts at or above the goal rate. An average of two or more shift rates during a time period can also be used to establish certification ratings e.g., one-third of the best shifts during a month are averaged—a rate of 6.0 to 8.0 for "Proficiency" and over 8.0 for "Excellence." Other criteria and time periods can be used to establish certification levels as well. Users can request and/or be provided with an electronically generated certificate that can be electronically issued to users, for example as shown in FIG. 16.

The examples discussed herein may assist in improving hand hygiene behavior by (1) providing a safe and anonymous method for health care providers to manage their own hand hygiene, (2) giving the health care provider regular feedback of their hand hygiene performance in the form of a hand hygiene rate, which can be visible to the users on the dispensers, posted online, sent to the user etc., and/or (3) providing coaching in the form of (a) encouragement of good performance, (b) reminders regarding lapses in hand hygiene performance, and/or (c) remediation and accountability for poor performance. Additionally, the examples discussed herein can give leadership and management the opportunity to be involved to encourage health care professionals to practice good hand hygiene.

III. Features of Hand Hygiene Compliance Method According to Examples of the Disclosure In an exemplary embodiment, a method may include tracking the dispensing of a plurality hand hygiene dispensers having hand sanitizer and each hand hygiene dispenser being associated with an individual user. The method can include one or more of the following steps: determining by a processor dispensing rates of the plurality of hand hygiene dispensers for a plurality of predetermined time periods; identifying each of the plurality of the hand hygiene dispensers with an individual user; determining by a processor a predetermined number of highest dispensing rates out of the plurality of predetermined time periods and calculating an average dispensing rate based on the predetermined number of highest dispensing rates; displaying the dispensing rates of the plurality of hand hygiene dispensers; and notifying an individual user regarding the individual user's performance In another exemplary embodiment, the method can include the following steps: displaying the individual user's dispensing results on a screen of the user's hand hygiene dispenser, and reviewing the dispensing of one or more of the plurality of hand hygiene dispensers over a predetermined time period to determine whether one or more of the plurality of hand hygiene dispensers has a higher dispensing rate to detect cheating by the user. The plurality of hand hygiene dispensers each have a wireless transmitter, and the wireless transmitter can transmit dispensing data.

The method may also include detecting whether the user is using an appropriate amount of hand sanitizing solution. In one example, the plurality of hand hygiene dispensers can each have a reservoir, and the number of dispenser activations are detected and compared with an amount of hand sanitizer in the reservoir to determine if an appropriate amount of sanitizer is being used by the user. The plurality of hand hygiene dispensers may be provided with an indicator that signals when the user dispenses hand sanitizer. The predetermined time periods may, in one example, include work shifts for the users, and the number of predetermined time periods may be greater than or equal to six. The predetermined number of highest dispensing rates can be greater than three. The method may further include assigning a rating to each individual user based on the user's average dispensing rate and can include providing the user with a predetermined message based on certain ratings of the user.

In another exemplary embodiment, an apparatus can include a processor for executing computer-executable instructions; and one or more memories storing the computer-executable instructions that, when executed, cause the apparatus to perform a method. The method may include one or more of the following steps: determining by a processor dispensing rates of the plurality of hand hygiene dispensers for a plurality of predetermined time periods; identifying each of the plurality of the hand hygiene dispensers with an individual user; calculating an average dispensing rate based on a predetermined number of dispensing rates; displaying the dispensing rates of the plurality of hand hygiene dispensers; and sending a notification to an individual user regarding the individual user's hand hygiene performance. The notification could inform the individual user that his/her average dispensing rate falls below a target threshold rate. In addition or alternatively, the notification could be associated with exemplary performance of hand hygiene. The method can also include displaying the individual user's dispensing rate on a screen of the user's hand hygiene dispenser and/or reviewing the dispensing of one or more of the plurality of hand hygiene dispensers over a predetermined time period to determine whether one or more of the plurality of hand hygiene dispensers has a higher dispensing rate to detect cheating by the user.

In one example, the plurality of hand hygiene dispensers can each have a RF transmitter, and the RF transmitter signals that the dispenser has been actuated or may transmit performance data to a centralized tracking system. The apparatus further comprises detecting whether the user is using an appropriate amount of hand sanitizing solution. The plurality of hand hygiene dispensers can each have a reservoir, and the number of dispenser activations can be detected and compared with an amount of hand sanitizer in the reservoir to determine if an appropriate amount of sanitizer is being used by the user. The plurality of hand hygiene dispensers can be provided with a visual, audible or tactile indicator that indicates when the user dispenses hand sanitizer and the event has been transmitted to the computer system. The apparatus can further include assigning a rating to each individual user based on the user's average dispensing rate and providing the user with a predetermined message based on certain ratings of the user. The dispensing of hand hygiene solution could also be stored in the dispenser computer for download at a later time.

In another exemplary embodiment, a computer program product, may include a computer usable medium having a computer readable program code embodied therein, the computer readable program code may be adapted to be executed by a processor to implement a method. The method may include one or more of the following steps: determining by a processor dispensing rates of the plurality of hand hygiene dispensers for a plurality of predetermined time periods; identifying each of the plurality of the hand hygiene dispensers with an individual user; calculating an average dispensing rate based on a predetermined number of dispensing rates; displaying the dispensing rates of the plurality of hand hygiene dispensers; and notifying an individual user if the average dispensing rate falls below a target threshold rate.

The computer program can also include instructions for displaying the individual user's dispensing rate on a screen of the user's hand hygiene dispenser and/or reviewing the dispensing of one or more of the plurality of hand hygiene dispensers over a predetermined time period to determine whether one or more of the plurality of hand hygiene dispensers has a higher dispensing rate to detect cheating by the user. The computer program product can further include detecting whether the user is using an appropriate amount of hand sanitizing solution. The plurality of hand hygiene dispensers can each have a reservoir, and the number of dispenser activations may be detected and compared with an amount of hand sanitizer in the reservoir to determine if an appropriate amount of sanitizer is being used by the user. The computer program product can also include instructions for assigning a rating to each individual user based on the user's average dispensing rate.

In another example, a computer-implemented method for tracking dispensing of a plurality hand hygiene dispensers having hand sanitizer each hand hygiene dispenser being associated with an individual user may include determining by a processor user IDs and associating the user IDs with the plurality of hand hygiene dispensers; displaying anonymously each user ID to each user; determining by a processor dispensing rates of the plurality of hand hygiene dispensers; displaying the dispensing rates of the plurality of hand hygiene dispensers; and sending a notification to an individual user regarding the individual user's hand hygiene performance. The notification may be provided anonymously to the user using the individual user's user ID. A real-time reminder can be sent after a predetermined time period when one of the plurality of dispensers are electronically detected within a predetermined area and when not used within predetermined time period. The predetermined time period can be based on usage patterns established by exemplary user hand hygiene data. The exemplary hand hygiene data can be based on position, setting, and duties of the user.

The embodiments disclosed herein can be applied within hospitals and other healthcare institutions of various sizes including, for example, clinics, doctor's offices, kiosks, or temporary set-ups (e.g. stores or shopping malls) for tasks as simple as shots for influenza or cholesterol screenings. While some of these settings might not be required to comply with regulatory hand washing protocols or compliance requirements, the embodiments disclosed herein may be useful in these environments. Another example is setups for handling disasters, epidemics or other circumstances in which large outdoor areas are dedicated, at least on a temporary basis, to treat a variety of patients. For certain types of treatment, it may be important for healthcare workers to comply with strict hand washing guidelines and to monitor compliance in a real-time basis.

It is contemplated that the embodiments and concepts disclosed herein could also be implemented outside of hospitals and other healthcare institutions in arenas where hand hygiene is important to prevent transmission of diseases. For example, the embodiments disclosed herein could also be implemented in the food service industry, the food processing industry, etc.

In another example, a system may include a plurality of hand hygiene dispensers, where each hand hygiene dispenser can include a housing configured to receive a container adapted to store hand sanitizer. The housing may include an input for detecting hand sanitizing events when hand sanitizer is dispensed from the container, and the input may be located within the housing. The housing may also include a memory for storing hand sanitizing events, and an accelerometer for recording motion information and for determining whether the hand hygiene dispenser is in use. Each hand hygiene dispenser may be configured to communicate to a network via a low energy transmission protocol.

In one example, the container can be configured to be squeezed to dispense sanitizer and to actuate the input within the housing. The container may define a wall, the wall can be placed adjacent the input such that the wall contacts the input and actuates the input when the user dispenses the hand sanitizer stored within the container. Each of the hand hygiene dispensers may include a display for displaying hand hygiene data. In one example, the low energy transmission protocol can be low energy Bluetooth.

The system may also include a plurality of computing devices where each computing device can include a display and may be configured to receive data from the plurality of hand hygiene dispensers regarding when one or more hand sanitizing events have occurred via the low energy transmission protocol and to display hand hygiene data. Each of the hand hygiene dispensers can be configured to send the hand sanitizing events stored on the memory to one of the computing devices when the hand hygiene dispensers are within a predetermined range of the one of the computing devices.

Additionally, the system can include a calculation module which can be configured to perform a method comprising: determining by a processor a dispensing rate of one or more of the plurality of hand hygiene dispensers for one or more predetermined time periods, and calculating an average dispensing rate based on a predetermined number of dispensing rates. The calculation module can be configured to send a notification to an individual user regarding the individual user's hand hygiene performance. For example, the calculation module can be configured to send a notification to one or more of the hand hygiene dispensers for displaying the notification. Additionally, the calculation module can be configured to identify each of the plurality of the hand hygiene dispensers with an individual user. The calculation module can reside on the plurality of hand hygiene dispensers, on the plurality of computing devices, or at a remote location on the network or internet. The calculation module can also be configured to review the dispensing of one or more of the plurality of hand hygiene dispensers over a predetermined time period to determine whether one or more of the plurality of hand hygiene dispensers has a higher dispensing rate to detect cheating by the user. The calculation module can be configured to detect whether an appropriate amount of hand sanitizing solution is used. The motion information from the accelerometer can be used to identify motion and hand hygiene patterns, and the motion and hand hygiene patterns can be used to create templates for evaluating hand hygiene data.

In another example, a method may include one or more of: providing a plurality of hand hygiene dispensers, providing each hand hygiene dispenser with a housing configured to receive a container adapted to store hand sanitizer, providing the housing with an input for detecting hand sanitizing events when hand sanitizer is dispensed from the container, placing the input within the housing, providing a memory for storing hand sanitizing events, placing an accelerometer for determining whether the hand hygiene dispenser is in use in the housing, and configuring each hand hygiene dispenser to communicate via a low energy transmission protocol. The method can also include configuring the container to be squeezed to dispense sanitizer and to actuate the input within the housing, providing the container with a wall, the wall being placed adjacent the input such that the wall contacts the input and actuates the input when the user dispenses the hand sanitizer stored within the container, providing each of the hand hygiene dispensers with a display for displaying hand hygiene data, and configuring the low energy transmission protocol as low energy Bluetooth.

The example method may also include one or more of: providing a plurality of computing devices, configuring each computing device to receive data from the plurality of hand hygiene dispensers regarding when one or more hand sanitizing events have occurred via the low energy transmission protocol, configuring each of the hand hygiene dispensers to send the hand sanitizing events stored on the memory to one of the computing devices when the hand hygiene dispensers are within a predetermined range of the one of the computing devices.

The method can also include configuring a calculation module to determine by a processor a dispensing rate of one or more of the plurality of hand hygiene dispensers for one or more predetermined time periods, calculating an average dispensing rate based on a predetermined number of dispensing rates, to send a notification to an individual user regarding the individual user's hand hygiene performance, to identify each of the plurality of the hand hygiene dispensers with an individual user. The method may also include placing the calculation module on the plurality of hand hygiene dispensers, on the plurality of computing devices, or at a remote location. The method can also include using the motion information to identify motion and hand hygiene patterns, and using the motion and hand hygiene patterns to create templates for evaluating hand hygiene data.

Aspects of the disclosure may be provided in a computer-readable medium having computer-executable instructions to perform one or more of the process steps described herein.

Aspects of the disclosure have been described in terms of illustrative embodiments thereof. Numerous other embodiments, modifications and variations within the scope and spirit of the disclosure will occur to persons of ordinary skill in the art from a review of this entire disclosure. For example, one of ordinary skill in the art will appreciate that the steps illustrated in the illustrative figures may be performed in other than the recited order, and that one or more steps illustrated may be optional in accordance with aspects of the disclosure.

We claim:

1. A system comprising:
   a plurality of hand hygiene dispensers, each hand hygiene dispenser comprising a housing configured to receive a container adapted to store hand sanitizer, the housing comprising an input for detecting hand sanitizing events when hand sanitizer is dispensed from the container, the input being located within the housing, a memory for storing hand sanitizing events, and an accelerometer for recording motion information in the memory;
   a plurality of computing devices, each computing device having a display, each computing device configured to receive data from the plurality of hand hygiene dispensers regarding when one or more hand sanitizing events have occurred; and
   a calculation module configured to perform a method comprising: determining by a processor a dispensing rate of one or more of the plurality of hand hygiene dispensers for one or more predetermined time periods and calculating an average dispensing rate based on a predetermined number of dispensing rates;
   wherein the calculation module is further configured to detect whether a predetermined amount of hand sanitizing solution is used and determine, for each hand hygiene dispenser and based on the motion information from the accelerometer of the hand hygiene dispenser, at least one of: a length of an evaluation period for one or more calculations, whether the hand hygiene dispenser is no longer in use, a number of steps taken by a user while carrying the hand hygiene dispenser, or whether a user is stationary for a predetermined amount of time in order to send a reminder signal to the user to dispense hand sanitizer; and
   wherein detecting whether a predetermined amount of hand sanitizing solution is used comprises:
   detecting a number of dispenser activations;
   measuring, by a sensor in communication with the calculation module and disposed within the housing, an amount of hand sanitizing solution within the container; and
   comparing the number of dispenser activations with the measured amount of hand sanitizing solution in the container.

2. The system of claim 1 wherein the calculation module is configured to send a notification regarding the individual user's hand hygiene performance to one or more of the hand hygiene dispensers for displaying the notification.

3. The system of claim 1 wherein the calculation module is configured to identify each of the plurality of the hand hygiene dispensers with an individual user.

4. The system of claim 1 wherein the calculation module resides at one or more of the plurality of hand hygiene dispensers, the plurality of computing devices, or a remote location.

5. The system of claim 1 wherein the calculation module is configured to review the dispensing of one or more of the plurality of hand hygiene dispensers over a predetermined time period to determine whether one or more of the plurality of hand hygiene dispensers has a higher dispensing rate to detect cheating by a user.

6. The system of claim 1 wherein the container is configured to be squeezed to dispense sanitizer and to actuate the input within the housing.

7. The system of claim 6 wherein the container defines a wall, the wall being placed adjacent to the input such that the wall contacts the input and actuates the input when a user dispenses the hand sanitizer stored within the container.

8. The system of claim 1 wherein each of the hand hygiene dispensers include a display for displaying hand hygiene data.

9. The system of claim 1 wherein each hand hygiene dispenser is configured to communicate to a network via a low energy transmission protocol.

10. The system of claim 9 wherein the low energy transmission protocol is low energy Bluetooth.

11. The system of claim 1 wherein each of the hand hygiene dispensers are configured to send the hand sanitizing events stored on the memory to one of the computing devices when the hand hygiene dispensers are within a predetermined range of the one of the computing devices.

12. The system of claim 1 wherein the calculation module is further configured to determine motion patterns for a plurality of types of users based on the motion information.

13. The system of claim 1 wherein a processor is configured to provide an electronic certification based on a minimum number of shifts by a user and a ratio of shift use rates at or above a predetermined goal rate.

14. A method comprising:
providing a plurality of hand hygiene dispensers, providing each hand hygiene dispenser with a housing configured to receive a container adapted to store hand sanitizer, providing the housing with an input for detecting hand sanitizing events when hand sanitizer is dispensed from the container, placing the input within the housing, providing a memory for storing hand sanitizing events, providing an accelerometer in the housing for recording motion information in the memory, and configuring each hand hygiene dispenser to communicate to a network via a low energy transmission protocol;
providing a plurality of computing devices, configuring each computing device to receive data from the plurality of hand hygiene dispensers regarding when one or more hand sanitizing events have occurred via the low energy transmission protocol; and
configuring a calculation module to determine a dispensing rate of one or more of the plurality of hand hygiene dispensers for one or more predetermined time periods and calculate an average dispensing rate based on a predetermined number of dispensing rates;
configuring the calculation module to detect whether a predetermined amount of hand sanitizing solution is used and determine, for each hand hygiene dispenser and based on the motion information from the accelerometer of the hand hygiene dispenser, at least one of: a length of an evaluation period for one or more calculations, whether the hand hygiene dispenser is no longer in use, a number of steps taken by a user associated with the hand hygiene dispenser, or whether to send a reminder signal to the user to dispense hand sanitizer; and
wherein configuring the calculation module to detect whether a predetermined amount of hand sanitizing solution is used comprises:
detecting a number of dispenser activations;
measuring, by a sensor in communication with the calculation module and disposed within the housing, an amount of solution within the container; and
comparing the number of dispenser activations with the measured amount of hand sanitizing solution in the container.

15. The method of claim 14 further comprising configuring the calculation module to send a notification to an individual user regarding the individual user's hand hygiene performance.

16. The method of claim 14 further comprising configuring the calculation module to identify each of the plurality of the hand hygiene dispensers with an individual user.

17. The method of claim 14 further comprising placing the calculation module at one or more of the plurality of hand hygiene dispensers, the plurality of computing devices, or a remote location.

18. The method of claim 14 further comprising configuring the container to be squeezed to dispense sanitizer and to actuate the input within the housing.

19. The method of claim 18 further comprising providing the container with a wall, the wall being placed adjacent the input such that the wall contacts the input and actuates the input when a user dispenses the hand sanitizer stored within the container.

20. The method of claim 14 further comprising providing each of the hand hygiene dispensers with a display for displaying hand hygiene data.

21. The method of claim 14 further comprising configuring the low energy transmission protocol as low energy Bluetooth.

22. The method of claim 14 further comprising configuring each of the hand hygiene dispensers to send the hand sanitizing events stored on the memory to one of the computing devices when the hand hygiene dispensers are within a predetermined range of the one of the computing devices.

23. The method of claim 14 further comprising configuring the calculation module to determine motion patterns for a plurality of types of users based on the motion information.

24. The method of claim 14 further comprising providing an electronic certification based on a minimum number of shifts by a user and a ratio of shift use rates at or above a predetermined goal rate.

* * * * *